United States Patent
Geebelen

(10) Patent No.: US 10,123,807 B2
(45) Date of Patent: Nov. 13, 2018

(54) ADAPTIVE SURFACE SURGICAL GUIDING APPARATUSES INCLUDING STABILITY AND/OR VERIFICATION ELEMENTS

(71) Applicant: Materialise N.V., Leuven (BE)

(72) Inventor: Benjamin Geebelen, Leuven (BE)

(73) Assignee: MATERIALISE, NV, Leuven (BE)

( * ) Notice: Subject to any disclaimer, the term of this patent is extended or adjusted under 35 U.S.C. 154(b) by 0 days.

(21) Appl. No.: 15/236,451

(22) Filed: Aug. 14, 2016

(65) Prior Publication Data

US 2016/0367264 A1 Dec. 22, 2016

Related U.S. Application Data

(63) Continuation of application No. PCT/EP2015/053055, filed on Feb. 13, 2015.

(30) Foreign Application Priority Data

Feb. 13, 2014 (GB) .................................. 1402563.9

(51) Int. Cl.
| | |
|---|---|
| *A61B 17/15* | (2006.01) |
| *A61B 17/17* | (2006.01) |
| *A61B 17/56* | (2006.01) |
| *A61B 34/10* | (2016.01) |

(52) U.S. Cl.
CPC .......... *A61B 17/154* (2013.01); *A61B 17/155* (2013.01); *A61B 17/1764* (2013.01); *A61B 17/56* (2013.01); *A61B 34/10* (2016.02); *A61B 2017/568* (2013.01); *A61B 2034/105* (2016.02); *A61B 2034/108* (2016.02)

(58) Field of Classification Search
CPC ............ A61B 17/1754; A61B 17/1755; A61B 17/1756; A61B 17/1764
USPC ............................... 606/87–88, 96, 300–321
See application file for complete search history.

(56) References Cited

U.S. PATENT DOCUMENTS

| | | | | |
|---|---|---|---|---|
| 2007/0239159 A1* | 10/2007 | Altarac | ................ | A61B 17/025 606/86 A |
| 2009/0228047 A1* | 9/2009 | Derouet | ............. | A61B 17/1686 606/286 |
| 2009/0318927 A1* | 12/2009 | Martin | ............... | A61B 17/1764 606/96 |

(Continued)

FOREIGN PATENT DOCUMENTS

| | | |
|---|---|---|
| WO | 2002/036032 A1 | 5/2002 |
| WO | 2009/001083 A1 | 12/2008 |

(Continued)

*Primary Examiner* — Matthew Lawson
(74) *Attorney, Agent, or Firm* — Patterson & Sheridan LLP

(57) ABSTRACT

The present application relates to adaptive surface surgical guiding apparatuses, tools, devices, or guides including stability and/or verification elements for use in surgical applications. In one embodiment, a surgical guiding apparatus comprises one or more rigid portions configured to attach to a first region of an underlying anatomical surface; a variable deformable portion coupled to the one or more rigid portions, the variable deformable portion configured to conform to a shape of a second region of the underlying anatomical surface; and a soft-tissue piercing element configured to pierce soft-tissue overlying a third region of the underlying anatomical surface and to attach to the underlying anatomical surface.

18 Claims, 14 Drawing Sheets

(56) References Cited

U.S. PATENT DOCUMENTS

| | | | |
|---|---|---|---|
| 2012/0172936 A1* | 7/2012 | Horrell | A61B 17/0401 606/319 |
| 2012/0179147 A1* | 7/2012 | Geebelen | A61B 17/17 606/1 |
| 2013/0317510 A1* | 11/2013 | Couture | A61B 17/154 606/88 |
| 2014/0018813 A1* | 1/2014 | McKinnon | A61B 17/155 606/88 |
| 2014/0163564 A1* | 6/2014 | Bollinger | A61B 17/1666 606/91 |

FOREIGN PATENT DOCUMENTS

| | | | | |
|---|---|---|---|---|
| WO | 2011/029911 A1 | 3/2011 | | |
| WO | 2011/156748 A2 | 12/2011 | | |
| WO | WO 2012/027402 | * 3/2012 | | A61B 17/56 |
| WO | 2013/043640 A1 | 3/2013 | | |

\* cited by examiner

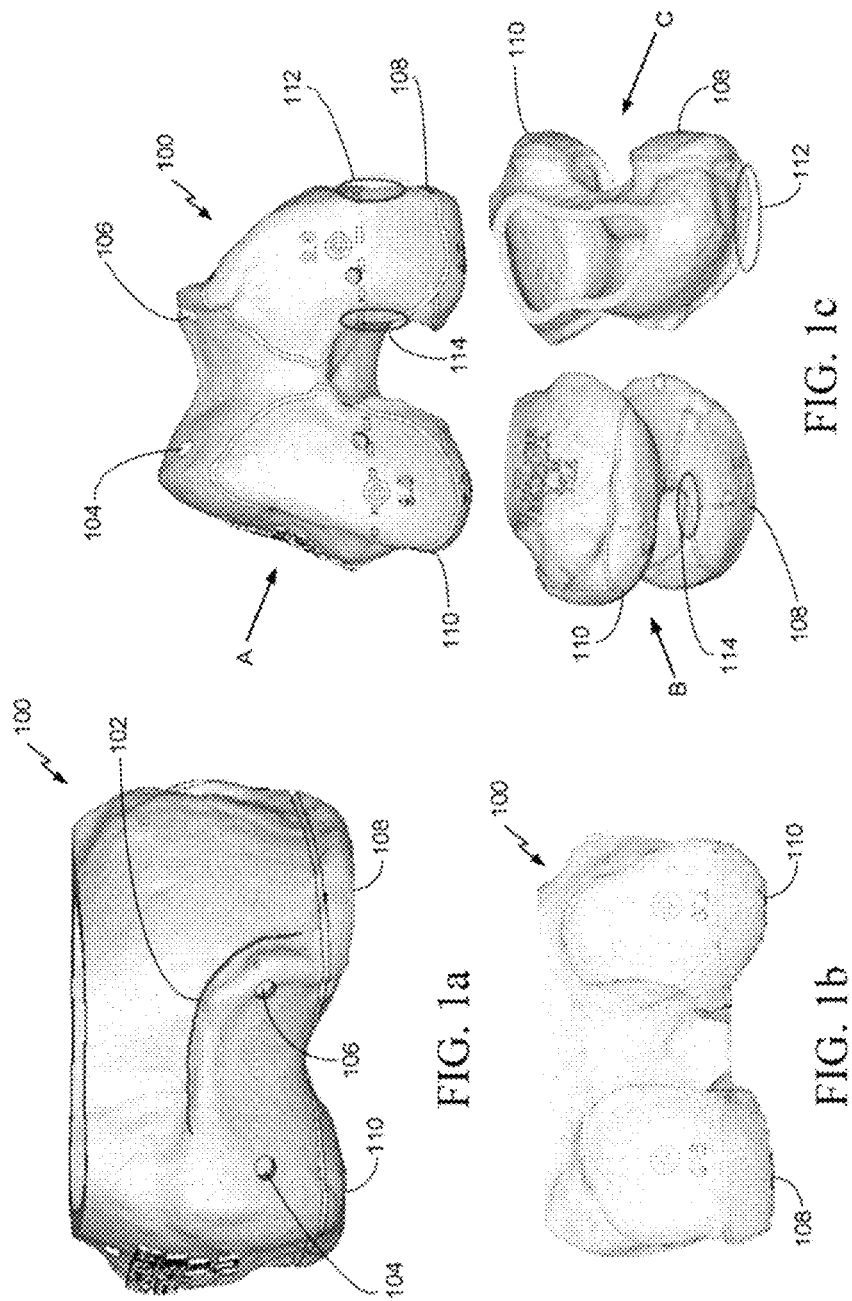

ADAPTIVE SURFACE SURGICAL GUIDING APPARATUSES INCLUDING STABILITY AND/OR VERIFICATION ELEMENTS

CROSS REFERENCES TO RELATED APPLICATIONS

This application is a continuation under 35 U.S.C. § 120 of International Application No PCT/EP2015/053055, filed Feb. 13, 2015 (published by the International Bureau as WO 2015/121400 on Aug. 20, 2015), which claims priority to GB Application No. 1402563.9, filed Feb. 13, 2014. Each of the above-referenced patent applications is hereby incorporated by reference in its entirety.

BACKGROUND

The present application relates to adaptive surface surgical guiding apparatuses, tools, devices, or guides (hereinafter "apparatus" or "apparatuses") including stability and/or verification elements for use in surgical applications. This application also relates to methods for manufacturing the adaptive surface surgical guiding apparatus including stability and/or verification elements and methods for using the adaptive surface surgical guiding apparatus including stability and/or verification elements in surgery.

Surgical guiding apparatuses have wide applications in orthopedic surgery. Surgical guiding apparatuses may allow a pre-operative surgical plan to be accurately implemented in the operating room. Further, surgical guiding apparatuses may help guide a surgical instrument, such as a cutting or drilling instrument, along a pre-defined cutting or drilling path.

However, creating a surgical guiding apparatus that includes one or more representations of an anatomical surface using pre-operative medical imaging data may not always be possible. For example, various anatomical surfaces may include soft-tissue that is not visible in certain types of medical images, like X-ray images. Additionally, anatomical surfaces may vary in shape from what is seen in the medical images. Finally, modeling errors may lead to representations that vary from the underlying anatomical surface. As a result, a surgical guiding apparatus may not fit well on a patient's anatomical surface(s) and may be unstable as a result. An unstable surgical guiding apparatus may lead to an inaccurate guiding position for a surgical instrument, which is undesirable.

In addition to the difficulty of creating surgical guiding apparatuses that include exact representations of anatomical surfaces, the underlying anatomical surfaces themselves may lack surfaces usable for stabilizing a surgical guiding apparatus. For example, the underlying anatomical surfaces themselves may not be conducive to supporting a surgical guiding apparatus. Similarly, the underlying anatomical surface may be covered by soft-tissues, which may prevent the surgical guiding apparatus from securely attaching to the underlying anatomical surface.

In light of these and other deficiencies, there is a need for adaptive surface surgical guiding apparatuses including stability and/or verification elements that provide secure and stable attachment to an anatomical surface.

SUMMARY

Various implementations of systems, methods and devices within the scope of the appended claims each have several aspects, no single one of which is solely responsible for the desirable attributes described herein. Without limiting the scope of the appended claims, some prominent features are described herein.

The present application relates generally to surgical guiding apparatuses that may be patient-specific. Details of one or more implementations of the subject matter described in this specification are set forth in the accompanying drawings and the following description. Other features, aspects, and advantages will become apparent from the description, the drawings, and the claims.

One aspect of the subject matter described in the disclosure provides a surgical guiding apparatus. The surgical guiding apparatus comprises one or more rigid portions configured to attach to a first region of an underlying anatomical surface; a variable deformable portion coupled to the one or more rigid portions, the variable deformable portion configured to conform to a shape of a second region of the underlying anatomical surface; and a soft-tissue piercing element configured to pierce soft-tissue overlying a third region of the underlying anatomical surface and to attach to the underlying anatomical surface.

BRIEF DESCRIPTION OF THE DRAWINGS

The following description of the figures is merely exemplary in nature and is not intended to limit the present teachings, their application, or their uses. Throughout the drawings, corresponding reference numerals indicate like or corresponding parts and features. Note that the relative dimensions of the following figures may not be drawn to scale.

FIG. 1*a* illustrates an exemplary anterior view of a femur.

FIG. 1*b* illustrates an exemplary posterior view of the femur of FIG. 1*a*.

FIG. 1*c* illustrates examples of alternative views of the femur of FIG. 1*a*, including a bottom view A, a bottom perspective view B, and a top perspective view C.

DETAILED DESCRIPTION

Figure 2C:
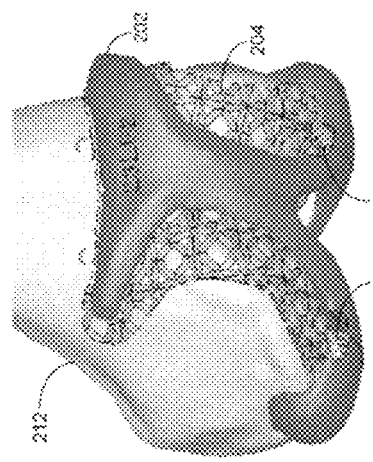
FIG. 2*c* illustrates an anterior perspective view of another example of a surgical guiding apparatus in accordance with some embodiments.

The following detailed description is directed to certain specific embodiments. However, the teachings herein can be applied in a multitude of different ways.

The present invention will be described with respect to particular embodiments, but the invention is limited only by the claims.

As used herein, the singular forms "a," "an," and "the" include both singular and plural referents unless the context clearly dictates otherwise.

The terms "comprising," "comprises," and "comprised of" as used herein are synonymous with "including," "includes," or "containing," "contains," and are inclusive or open-ended and do not exclude additional, non-recited members, elements or method steps. The terms "comprising," "comprises," and "comprised of" when referring to recited components, elements or method steps also include embodiments which "consist of" said recited components, elements or method steps.

Furthermore, the terms "first," "second," "third," and the like in the description and in the claims are used for distinguishing between similar elements and not necessarily for describing a sequential or chronological order, unless specified. It is to be understood that such terms are interchangeable under appropriate circumstances and that the embodiments of the invention described herein are capable of operation in sequences other than those described or illustrated herein.

Reference throughout this specification to "one embodiment," "an embodiment," "some aspects," "an aspect," or "one aspect" means that a particular feature, structure or characteristic described in connection with the embodiment or aspect is included in at least one embodiment of the present invention. Thus, appearances of the phrases "in one embodiment," "in an embodiment," "some aspects," "an aspect," or "one aspect" in various places throughout this specification are not necessarily all referring to the same embodiment or aspects. Furthermore, the particular features, structures or characteristics may be combined in any suitable manner in one or more embodiments or aspects, as would be apparent to a person skilled in the art from this disclosure. Furthermore, while some embodiments or aspects described herein include some but not other features included in other embodiments or aspects, combinations of features of different embodiments or aspects are meant to be within the scope of the invention. For example, in the appended claims, any of the features of the claimed embodiments or aspects can be used in any combination.

The present application discloses adaptive surface surgical guiding apparatus including stability and/or verification elements. One or more aspects of the surgical guiding apparatuses may be patient-specific. The surgical guiding apparatuses are designed to provide accurate and stable attachment to an underlying anatomical surface, such as a bone. Providing for an accurate and stable attachment to an anatomical surface allows for precise surgical procedures to be implemented, such as the precise introduction of a surgical instrument into a specific part of a bone. As used herein, the term "attach," "attachment," and/or any variation thereof, refers to placing, connecting, or contacting one object on or to another object. For example, a surgical guiding apparatus "being attached to a bone" (or other anatomical surface) may refer to the placement of the apparatus on the bone with the structure of the bone holding the apparatus in place. As another example, a surgical guiding apparatus "being attached to a bone" (or other anatomical surface) may also refer to attaching the apparatus to the bone using one or more clamps, screws, snaps, glues, and the like. As yet another example, a surgical guiding apparatus "being attached to a bone" (or other anatomical surface) may refer to attaching the apparatus to the bone using both placement and/or shape of the apparatus in addition to one or more attachment devices (e.g. clamps, screws, snaps, and the like).

In some embodiments, one or more aspects of a surgical guiding apparatus may be based on data relating to underlying anatomical surfaces of a patient (such as medical images) and are thus sometimes referred to as "patient-specific." The term "patient-specific," as used herein with reference to surgical apparatuses, may refer to aspects of surgical apparatuses, devices, tools, and/or guides that are designed based on an individual patient's anatomy in order to provide a custom fit and/or function for the particular patient. The patient-specific nature of the surgical guiding apparatus allows for a custom fit of the surgical guiding apparatus with the underlying patient anatomy and enhances the ability to perform precise surgical procedures on the patient. Thus, the use of patient-specific devices, tools, or guides allows for improved surgical interventions, orthopedic structures, and/or kinematics for the patient. Additionally, similar benefits may be obtained when patient-specific apparatuses are used in combination with standard implants, tools, devices, surgical procedures, and/or other methods.

In some embodiments, patient-specific surgical guiding apparatuses may be based on pre-operative procedures. For example, pre-operative procedures can identify various regions of a specific patient's anatomy and determine, based on the identified regions of the anatomy, a patient-specific design for various surgical guiding apparatus components (e.g., flexible and/or rigid portions, deformable linkages, clamps, apertures, and the like). Pre-operative procedures can also determine preferred locations on the patient's anatomy for attaching a surgical guiding apparatus based on the identified regions of the patient's anatomy.

Pre-operative procedures may involve obtaining an image of a patient's anatomy prior to performing surgery. Digital patient-specific image information may be provided by any suitable means known in the art, such as, for example, an X-ray machine, a computer tomography (CT) scanner, a magnetic resonance imaging (MRI) scanner, an ultrasound scanner, and the like. For example, pre-operative planning may include the construction of a two-dimensional (2-D) image or a three-dimensional (3-D) virtual model of an anatomical object, surface, or other part thereof.

A 3-D virtual model of a patient's anatomical surface may be created from 2-D images, such as X-rays, using statistical methods described in further detail below. In some embodiments, construction of the 3-D virtual model of an anatomical object may begin with scanning a patient. Scanning may include using a scanning technique that generates medical imaging data, such as a CT scan, a MRI scan, or the like. In some embodiments, the output of the scan may include a stack of 2-D slices forming a 3-D data set. The output of the scan may be digitally imported into a computer program and may be converted to a 3-D computer model of an anatomical object using statistical algorithms known in the field of image processing technology. For example, the virtual 3-D model may be constructed from the data set using a computer program such as Mimics™ as supplied by Materialise N.V., Leuven, Belgium.

In some embodiments, a simulated model may be used in a fitting method to create a 3-D virtual model of an anatomical object based on 2-D image segments of the anatomical object, such as a bone. For example, a simulated model of an anatomical object may be compared with medical images of a patient's anatomy in order to generate a 3-D model of the patient's anatomy. As discussed above, the medical images may include CT scan images, X-ray images, MRI images, and the like.

A simulated model of an anatomical object may be used because one or more medical images of a patient's anatomy alone may not include sufficient information to build a reliable 3-D model of the patient's underlying anatomy. Accordingly, in order to build up a reliable 3-D model, the simulated model, including anatomical knowledge relating to the object in the medical image, may be used to interpret the image. For example, a simulated model may include a statistical shape model (SSM) and the anatomical knowledge may be condensed in the SSM for representing the anatomical object. The SSM may be a 2-D or 3-D model and may correspond to a theoretical expected object with similar characteristics as those of a patient's anatomy (e.g. a patient's bone). Thus, a SSM may be used in a fitting method to generate a 3-D model of a patient's anatomy by comparing and fitting the SSM to the one or more medical images of a patient's anatomy.

In some embodiments, an iterative closest point process, or a variant thereof, may be used for generating a 3-D model of a patient's anatomy. For example, the comparison or fit of the SSM to the one or more medical images of a patient's anatomy may be done by aligning the SSM with an anatomical object in the medical images. The alignment may be done, for example, by selecting points matching various data points on the SSM with data points on the medical image. Various matching methods may be used. For example, matching may be done by determining the nearest points on the medical image relative to related points on the SSM. Further, various translations and rotations of the SSM may be tested relative to the medical image in order to match corresponding points, features, etc., and to align the SSM and the medical image data. The process may iteratively select and match points on the SSM and the medical image and minimize the distance between corresponding points on the SSM and the medical image in order to refine the 3-D model of a patient's anatomy. The result of the alignment process is an accurate 3-D model of an anatomical object.

In some embodiments, the 3-D model of an anatomical object may be generated based on 3-D imaging techniques, such as segmentation of 3-D image data to create the 3-D model. For example, various 3-D images of the anatomical object may be obtained (e.g., by magnetic resonance imaging (MRI) or computed tomography (CT) imaging) and segmented in order to create the 3-D model. In some aspects, the 3-D model may be based on a 3-D reconstruction of CT or MRI images.

Once the 3-D model of an anatomical object, such as a bone or a part thereof, is reconstructed, the preferred position, orientation, and specific surgical parameters that are needed for the surgery may be defined. For example, the depth and diameter of bores and drill paths on a bone may be defined. Based on the 3-D model of the bone, a surgical guiding apparatus can be designed, manufactured, and/or manipulated to meet the needs of the specific patient.

Creating an accurate representation of a patient's anatomy using pre-operative medical imaging data is not always possible. For example, one or more regions of an anatomical object (such as a bone) may include soft-tissue (e.g., cartilage, muscles, tendons, ligaments, and the like), which may not be visible using certain medical imaging methods. For example, cartilage may not be visible in X-ray and CT images. But soft-tissues, such as cartilage, may cover much of a region where an operation is needed. While soft-tissue thickness may be estimated, the estimates may not be accurate enough to use these soft-tissue regions for attachment points for a surgical guiding apparatus. As a result, it may not be possible to locate an optimal position or region on an anatomical surface (such as a bone) for attachment of the surgical guiding apparatus due to the limited regions of the bone that are visible in the medical image(s).

Furthermore, anatomical surfaces may vary in shape from what is seen in the medical images. As a result, surgical guiding apparatuses designed based on such medical images may be less stable while in use. Similarly, the anatomical surface depicted in a 3-D model created using the statistical modeling methods described above may include regions of variable accuracy, due to various types of error in the modeling process (described in further detail below). Accordingly, a rigid surgical guide created based on medical imaging and/or statistical modeling may have variable gaps when attached to a patient's anatomy due to the inaccurate modeling and may thus have an unstable fit when attached to the patient's anatomy. For example, when part of an underlying anatomy is not visible in an image (e.g., due to soft-tissue regions in the bone), a fulcrum point may be present in the actual anatomical surface over which a rigid guide may hinge, thereby creating an unstable and/or rocking fit while in use.

An accuracy map may be generated and used to determine the accuracy of different regions of a modeled anatomical object. An accuracy map provides an indication of how accurate or certain the modeling result is at each point of a model of an anatomical object (such as a 3-D model) and may indicate the confidence of each point of the surface. In some embodiments, a standard deviation ($\sigma$) may be used to model the accuracy, and the accuracy map may indicate the standard deviation at each point.

As described above, there are several sources of error that may occur in the generation of the 3-D model, and thus there may be several different accuracy maps. One example of a source of error is error in the input data, such as image data that may have a limited accuracy due to the nature of obtaining and measuring the data (e.g., limits on the accuracy of the imaging device, limits on the capabilities of the imaging device, and the like). Another example of a source of error is inaccuracies caused by errors in fitting a simulated model relating to the anatomical object, such as an SSM, to the image data (e.g., misalignment of the SSM with the X-ray, incompleteness of the SSM itself, and the like). Yet another example of a source of error is inaccuracies caused by lack of data in the images (e.g., 2-D input image data may not provide enough data to accurately portray each component of an anatomical object). A fourth example of a source of error is incompleteness of the SSM itself, such as missing portions due to the SSM being condensed. Individual accuracy maps may be combined into one total accuracy map. The combined or individual accuracy maps contain an accuracy or certainty level at each point of a 3-D model of an anatomical surface, such as a bone.

As indicated above, specific regions of an anatomical object (such as a bone) may comprise specific anatomical features that can be used to attach a surgical guiding apparatus. Patient-specific anatomical data (such as medical images) may be used in order to identify surfaces of a bone that are most suitable for attachment when designing a surgical guiding apparatuses. But as explained above, it may be difficult to create an accurate representation of an anatomical surface using pre-operative medical imaging data and/or statistical modeling. For example, an anatomical surface may include a highly variable surface that cannot be imaged accurately. As a result, despite being patient-specific, a surgical guiding apparatus may still not fit with the underlying anatomical surface in a secure and stable manner. Accordingly, an adaptive surface surgical guiding apparatus including deformable portions may be designed to securely attach to an anatomical surface despite the underlying accuracy of a model of the anatomical object.

In some embodiments, the deformability of a deformable portion of a surgical guiding apparatus varies among different points of the deformable portion in relation to an amount of variability of the underlying anatomical surface. In some embodiments, the deformability of a deformable portion may be relatively greater at points where the variability of the underlying anatomical surface and/or the inaccuracy of the model of the underlying anatomical surface is relatively greater. For example, a region of a bone may have a highly variable surface and may include large amounts of overlying soft-tissue that does not show up in a medical image. Consequently, the portion of the deformable portion designed to attach to that region of the bone may be highly deformable or flexible such that it can conform to the region despite the soft-tissue and/or the variable surface.

Additionally, in some embodiments, the deformability of a deformable portion of a surgical guiding apparatus may be specific to a given direction relative to the underlying anatomical surface. As one example, certain points of the variable deformable portion may only be compressible in a particular direction (e.g. perpendicular to the surface of an anatomical surface) and not in other directions. Accordingly, an adaptive surface surgical guiding apparatus may securely attach to uneven and/or variable surfaces of an anatomical object (such as a bone) even in the absence of an accurate image or model of the anatomical object.

A method of manufacturing an adaptive surface surgical guiding apparatus may include creating an adaptive surface surgical guiding apparatus design. The adaptive surface surgical guiding apparatus may be designed, for example, using medical images of a patient's anatomy and/or statistical modeling, as described above.

An adaptive surface surgical guiding apparatus design may include one or more rigid portions configured to attach to a first region of an underlying anatomical surface, and a variable deformable portion coupled to the rigid portion and configured to attach to a second region of the underlying anatomical surface. As described above, the term "attach," and/or any variation thereof, may refer to placing, connecting, or contacting a rigid portion or a deformable portion of a surgical guiding apparatus on or to an anatomical surface.

For example, a shape of a rigid portion may match the structure of an anatomical object (such as a bone) so that the rigid portion may be attached to a first region of the anatomical object by, for example, applying pressure on the rigid portion in the direction of the anatomical object. In another example, a rigid portion of a surgical guiding apparatus may be attached to an anatomical object (such as a bone) using an attachment device, such as one or more clamps, screws, snaps, glues, or the like.

A variable deformable portion may be configured to conform to a shape of a second region of an anatomical object (such as a bone) in order to provide a stable attachment of the surgical guiding apparatus to the anatomical object. For example, a variable deformable portion may be attached to a second region of the bone by, for example, applying pressure on the deformable portion in the direction of the anatomical object.

In some embodiments, a variable deformable portion may be designed to conform to a surface of an anatomical object as approximated and depicted in a model of the anatomical object (e.g., an SSM). Accordingly, in some embodiments, the variable deformable portion may not conform exactly to the underlying anatomical surface if one or more regions of the surface were not accurately modeled, but may be flexible enough to still provide secure and stable attachment to the anatomical surface.

Accordingly, surgical guiding apparatuses that include one or more adaptive surfaces that are able to provide a secure and stable attachment to the bone are desirable. An advantage of the surgical guiding apparatuses described in the present application provides that sufficient information may be obtained for designing a surgical guiding apparatus for secure and stable placement onto an anatomical surface of a patient based on any type of imaging and/or modeling technology and based on any underlying anatomical surface.

FIG. 1a illustrates an anterior view of one example of a femur 100. While the description herein describes the femur 100, it will be apparent to one of skill in the art that the content of this disclosure applies equally to other bones, such as the humerus, scapula, tibia, fibula, talus, and other shoulder, hip, ankle, and/or finger bones. The anterior region illustrated in FIG. 1a is located at the distal end of the femur 100. This anterior region of the femur 100 may include a portion 102 that may be used to attach and secure a surgical guiding apparatus thereto. For example, an osteophyte is a bony projection that forms along bones, such as at a joint, and may occur in patients with arthritis. One or more osteophytes projecting from the surface of the femur 100 may provide a surface upon which a surgical guiding apparatus may be attached (in whole or in part). As another example, a medial condyle 108 and a lateral condyle 110 are located at the distal end of the femur 100, and may also be used for attaching a surgical guiding apparatus thereto. Additionally, holes 104 and 106 may be created using a surgical device (e.g., a surgical drill) inserted into one or more apertures of a surgical guiding apparatus.

FIG. 1b illustrates an exemplary posterior view of the femur 100 of FIG. 1a. FIG. 1b illustrates the medial condyle 108 and the lateral condyle 110 located at the distal end of the femur 100. FIG. 1c illustrates examples of alternative views of the femur 100 illustrated in FIG 1a, including a bottom view A, a bottom perspective view B, and a top perspective view C. In particular, FIG. 1c illustrates the medial condyle 108 and the lateral condyle 110 located at the distal end of the femur 100. The medial 108 and lateral 110 condyles may provide one or more portions that may be used to attach and secure a surgical guiding apparatus thereto. For example, a lateral region 112 and a medial region 114 of the medial condyle 108 may be used to attach and secure a surgical guiding apparatus. In some embodiments, lateral and medial regions of the lateral condyle 110 may be used to attach and secure a surgical guiding apparatus. For example, lateral and medial regions of the lateral condyle 110 may be used in addition to the lateral region 112 and medial region 114 of the medial condyle 108 to attach a surgical guiding apparatus to the femur 100. As another example, only the lateral and medial regions of the lateral condyle 110 may be used as an alternative to the lateral region 112 and medial region 114 of the medial condyle 108. In some embodiments, osteophytes located on the medial condyle 108 and/or the lateral condyle 110 may be used to attach and secure a surgical guiding apparatus.

Figure 2D:
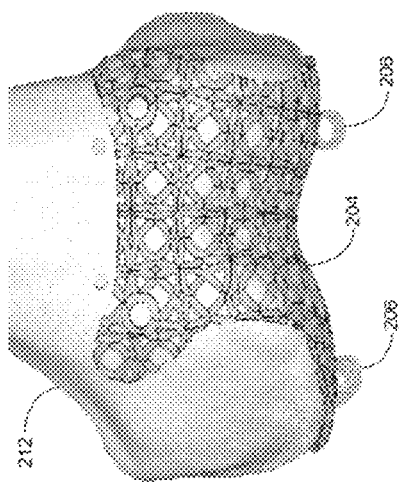
FIG. 2*d* illustrates an anterior view of an example of a variable deformable portion of the surgical guiding apparatus of FIG. 2*c* in accordance with some embodiments.
Figure 2A:
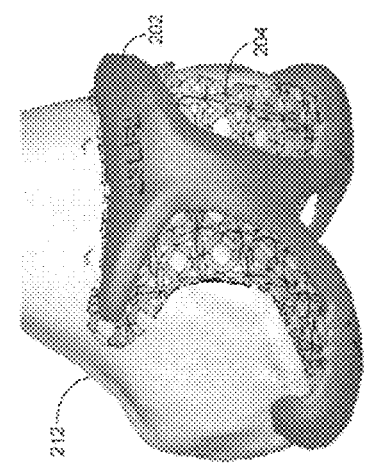
FIG. 2*a* illustrates an anterior perspective view of an example of a surgical guiding apparatus in accordance with some embodiments.

FIG. 2a illustrates an anterior perspective view of an example of an adaptive surface surgical guiding apparatus 200 configured to attach to a bone. In some embodiments, the adaptive surface surgical guiding apparatus 200 may be a femoral adaptive surface surgical guiding apparatus for attaching to a distal end of a femur 212. Notably, while the description herein relates to femur 212 as an example of an anatomical surface, it will be apparent to one of skill in the art that the content of this disclosure applies equally to other anatomical surfaces, such as a humerus, scapula, tibia, fibula, talus, spine, and other shoulder, hip, ankle, and/or finger bones. Additionally, an adaptive surface surgical guiding apparatus may also be designed to attach to other anatomical surfaces including external portions of a patient, such as an arm, leg, abdomen, back, foot, hand, or other body part.

The adaptive surface surgical guiding apparatus 200 includes an adaptive surface including a rigid portion 202 and a variable deformable portion 204 coupled to the rigid portion 202. In some embodiments, the rigid portion 202 and the variable deformable portion 204 may be manufactured as separate structures. In other embodiments, the rigid portion 202 and the variable deformable portion 204 may be manufactured as a single structure with varying thicknesses and patterns, for example, using the additive manufacturing techniques described below.

The rigid portion 202 of the adaptive surface surgical guiding apparatus 200 may be attached to a first portion of the femur 212. For example, the rigid portion 202 may be attached to the anterior region of the femur 212, as well as to the bottom portion of the femur 212 including the medial condyle 108 and the lateral condyle 110 (as illustrated in FIGS. 1a-c). In some embodiments, the rigid portion 202 is attached to the femur 212 by the variable deformable portion 204. For example, the variable deformable portion 204 may be attached to the femur 212, and the rigid portion 202 may be attached to the variable deformable portion 204. The rigid portion 202 may provide a strong attachment to well-defined regions of the femur 212. For example, the rigid portion 202 may be designed so that the rigid portion 202 does not easily flex when an object comes into contact with the rigid portion 202 or when the rigid portion 202 makes contact with the surface of the femur 212. Similarly, the rigid portion 202 may be designed to be stable enough so that a physician may operate through part of the rigid portion 202 without moving the rigid portion 202, such as when guiding a drill or other surgical instrument through an aperture in the rigid portion 202.

In some embodiments, the rigid portion 202 may be fixedly attached to the femur 212. In other embodiments, the rigid portion 202 may be attached to the femur 212 by resting on the femur 212. In these embodiments, as further described below, one or more clamps may be used to secure the adaptive surface surgical guiding apparatus 200 to the femur.

While only a single rigid portion is illustrated in FIG. 2a, it will be apparent to one of skill in the art that the adaptive surface surgical guiding apparatus 200 may include one or more rigid portions. In some embodiments, the adaptive surface surgical guiding apparatus 200 may include a plurality of rigid portions or structures, with one or more of the rigid portions attached to the femur 212 and one or more of the rigid portions that are not attached to the femur 212. For example, one or more of the rigid portions that are not attached to the femur 212 may be used to connect two or more rigid portions that are attached to the femur 212. In another example, one or more rigid apertures may be coupled to the rigid portion 202 and/or the variable deformable portion 204.

The well-defined regions of the femur 212 upon which the rigid portion 202 is designed to attach may be clear in medical images and may be accurately modeled using the pre-operative and statistical methods described above for designing the adaptive surface surgical guiding apparatus 200. As a result, the regions of a 3-D model of femur 212 corresponding to these well-defined regions may be used to accurately design the rigid portion 202 to attach to these regions with minimal or no error.

Figure 2B:
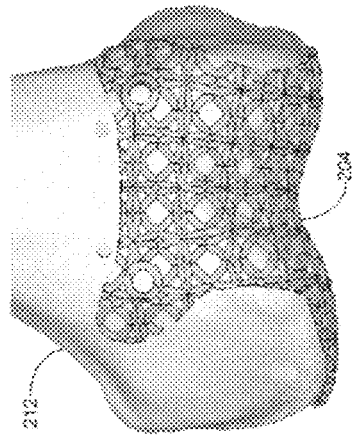
FIG. 2*b* illustrates an anterior view of an example of a variable deformable portion of the surgical guiding apparatus of FIG. 2*a* in accordance with some embodiments.

FIG. 2b illustrates an anterior view of an example of the variable deformable portion 204 of the adaptive surface surgical guiding apparatus 200. The variable deformable portion 204 may be designed to conform to a shape of the other regions of the femur 212 that are less well-defined and thus less accurately portrayed in the 3-D model of the femur 212. For example, the variable deformable portion 204 may be designed so that it may be deformed in three-dimensions relative to the femur 212. The less well-defined regions may be less accurately portrayed in the 3-D model due to lack of detail in a medical image (e.g., due to soft-tissue making up large portions of the femur 212, and the like), inaccuracies in the 3-D model, and the like. The variable deformable portion 204 is thus able to mate with the underlying, variable anatomical surface to create a stable fit and proper orientation for the adaptive surface surgical guiding apparatus 200. Thus, the stable portion 202 may attach to the more accurately modeled regions of the femur 212 in order to obtain the majority of the fit positioning, and the variable deformable portion 204 may attach to the more variable, less-defined regions in the 3-D model to achieve stability of the adaptive surface surgical guiding apparatus 200 in use.

In some embodiments, the variable deformable portion 204 increases surface contact with the underlying surface of the femur, and thus can be used to increase stability of the adaptive surface surgical guiding apparatus 200 without the risk of creating a fulcrum point. In some embodiments, the variable deformable portion 204 may conform to the anterior region of the femur 212 as well as to the bottom region of the femur 212, including the medial condyle 108 and the lateral condyle 110. In some embodiments, the variable deformable portion 204 conforms to a larger region of the anterior and bottom portions of the femur 212 than the rigid portion 202 because there is more area in these regions that are less well-defined and/or more variable.

The deformability and/or flexibility of the variable deformable portion 204 may vary at different points of the variable deformable portion 204 based on an amount of variability of the underlying surface of the femur 212. For example, each point on the variable deformable portion 204 may have a different deformability characteristic based on the point on the femur 212 for which it is designed to attach. The deformability and/or flexibility of the variable deformable portion 204 may increase at any given point as the variability or inaccuracy of the underlying anatomical surface increases. For example, a large region of the femur 212 may include soft-tissue that does not show up in a medical image. The same or a different region of the femur 212 may include a highly variable surface. The part of the variable deformable portion 204 that is designed to attach to that region of the femur 212 may thus be highly deformable or flexible so that it can conform to the variable surface and/or the soft-tissue region of the bone, as illustrated in FIG. 2b. As described in more detail below, different material thicknesses and/or patterns may be used to vary the flexibility of the variable deformable portion 204.

In some embodiments, the variable deformable portion 204 may be designed based on a best estimation of the expected underlying anatomical surface. For example, each point on the variable deformable surface 204 may be designed based on medical image data, statistical shape models, documented anatomic averages of the underlying surface, and/or one or more accuracy maps. An estimated anatomic model of variable accuracy may be used as an initial design point for the variable deformable surface 204. Due to the inaccuracy and/or variability of the estimated model of the underlying anatomical surface, the variable deformable surface 204 may be designed with varying flexibility, as described above, to conform to the surface.

An accuracy map may be used to determine a range of variability of the underlying anatomical surface of the femur 212. For example, a highly inaccurate point on the accuracy map for the 3-D model of the femur 212 may be correlated to a highly variable point on the surface of the femur 212 where the exact surface shape is unknown. The range of variability determined for the surface of the femur 212 may be used to create a variability map for the variable deformable portion 204. The variability map may include a deformability metric for each point of the variable deformable portion 204. The deformability metric for a given point on the variability map corresponds to the variability of a corresponding point on the surface of the femur 212. The variability map may then be applied to the variable deformable portion 204 so that each point of the deformable portion 204 is designed to be deformable in proportion to the deformability metric of a corresponding point on the variability map. Based on the application of the variability map, points of the variable deformable portion 204 designed to attach to inaccurately modeled and/or variable regions of the surface of the femur 212 may be highly deformable so that the variable deformable portion 204 will conform to the surface regardless of the variability of that surface.

In some embodiments, an accuracy map and a corresponding variability map may be used to design the rigid portion 202. For example, a rigid portion 202 of the adaptive surface surgical guiding apparatus 200 may be designed to attach to regions of the femur 212 that have highly accurate representations in the 3-D model, as indicated by high confidence levels in a corresponding accuracy map. The rigid portion 202 may then be attached to these regions of the femur 212 with high accuracy due to the accurate nature of the 3-D model for these regions.

The rigid portion 202 and the variable deformable portion 204 may include various materials that are selected based on their flexibility, sterilibility, biocompatibility, and/or other factors. For example, materials may include a hard plastic with flexible characteristics, such as a polyamide. As another example, the materials may include a rubber-like material, such as thermoplastic polyurethane. In some embodiments, the rigid portion 202 and the variable deformable portion 204 may be manufactured using the same materials. The rigid portion 202 may be manufactured with rigid characteristics by increasing the thickness of the rigid portion 202 until the portion 202 is not easily moveable. For example, the thickness of the rigid portion 202 may be designed so that the portion 202 does not easily flex when contact is made thereto or when the rigid portion 202 makes contact with the surface of the femur 212. The thickness of the rigid portion 202 may also be designed to be stable enough so that a physician may operate through part of the rigid portion 202 without moving the rigid portion 202, such as guiding a drill or other surgical instrument through an aperture in the rigid portion 202.

As noted above, the deformability and/or flexibility of the variable deformable portion 204 may vary at different points of the variable deformable portion 204 based on an amount of expected variability of the underlying surface of the femur 212. The varying deformability and/or flexibility may be achieved by varying the thickness and/or pattern of the material used to manufacture the variable deformable portion 204. For example, the variable deformable portion 204 may be manufactured to be thinner than the rigid portion 202 so that the deformable portion 204 is able to deform and flex with relative ease. The variable deformable portion 204 may deform upon making contact with the underlying surface of the femur 212 so that the deformable portion 204 conforms to the surface. In some embodiments, the pattern of the variable deformable portion 204 may also be designed so that the deformable portion 204 has particular flexible characteristics.

For example, the variable deformable portion 204 illustrated in FIG. 2b includes a plurality of holes through which the underlying anatomical surface of femur 212 is exposed. In some embodiments, the variable deformable portion 204 may be manufactured as a structure including one or more volumes filled with a space filling substance (e.g., air bubble, liquid bubble, etc.), a crystal lattice-like structure, one or more springs, and/or the like. The pattern of the holes, substance filled volumes, crystal lattice, springs, etc. allows further flexibility in addition to that provided by the thickness of the material used to manufacture the variable deformable portion 204. The holes may also allow a physician to observe the underlying anatomical surface of femur 212. The holes may be any shape, size, etc. in order to achieve a desired flexibility or design.

The thickness and pattern of the material along different regions of the variable deformable portion 204 may be designed so that varying flexibility may be achieved in the different regions. For example, regions of the variable deformable portion 204 that are designed to attach to less well-defined (e.g., inaccurately modeled) and/or highly variable regions of the femur 212 may include a certain thickness and pattern that provides higher flexibility than regions of the deformable portion 204 that are designed to attach to more well-defined and less variable regions of the femur 212.

In some embodiments, different materials may be used for the rigid portion 202 and the variable deformable portion 204. For example, a hard plastic may be used to manufacture the rigid portion 202 and a rubber or soft plastic may be used to manufacture the variable deformable portion 204. It will be apparent to one of skill in the art that the content of this disclosure applies equally to other materials that may be used to design and manufacture the rigid portion 202 and the variable deformable portion 204.

The rigid portion 202 depicted in FIG. 2a may be configured to overlap at least a part of the variable deformable portion 204. For example, the variable deformable portion 204 may conform to a larger region of the anterior and bottom portions of the femur 212 than the region upon which the rigid portion 202 can attach because there is more area in these regions that are less well-defined and/or more variable. In some embodiments, the rigid portion 202 attaches only to the well-defined regions of the femur 212, while the variable deformable portion 204 attaches to both the well-defined and not well-defined regions.

The variable deformable portion 204 may be coupled to the rigid portion 202 according to various embodiments. In some embodiments, the variable deformable portion 204 and the rigid portion 202 may be directly coupled with each other. In other embodiments, the variable deformable portion 204 and the rigid portion 202 may be coupled using at least one deformable linkage. For example, a deformable linkage may include a spring, a flexible clip, a flexible hinge, a flexible clamp, or any other flexible linkage that allows movement or adaptability in one or more directions.

FIG. 2c illustrates an anterior perspective view of another example of the adaptive surface surgical guiding apparatus 200 including two deformable linkages 206. The deformable linkages 206 are designed to deform in an up and down direction toward and away from the rigid portion 202, and optionally in a left and right direction, so that the fit of the adaptive surface surgical guiding apparatus 200 in the region with the deformable linkages can adapt to a variable underlying surface of the femur 212.

FIG. 2d illustrates an anterior view of the variable deformable portion 204 including the two deformable linkages 206. The deformable linkages 206 illustrated in FIGS. 2c and 2d include springs. One of skill in the art will understand that the deformable linkages may include any flexible linkage that allows movement or adaptability in one or more directions.

The variable deformable portion 204 and the rigid portion 202 may be coupled using at least one rigid linkage. In some embodiments, a rigid linkage may include a clip, hinge, clamp, or any other rigid device. In some embodiments, a rigid linkage may be made of materials that are not easily moveable based on, for example, their thickness.

In some embodiments, the variable deformable portion 204, the rigid portion 202, and the one or more deformable linkages may be manufactured as separate structures. In some embodiments, the variable deformable portion 204, the rigid portion 202, and the one or more deformable linkages may be manufactured as a single structure with varying thicknesses and patterns, for example, using the additive manufacturing techniques described below. For example, the entire adaptive surface surgical guiding apparatus 200 may be manufactured with varying thicknesses and patterns as a single structure using additive manufacturing so that individual parts do not need to be manufactured.

In some embodiments, the adaptive surface surgical guiding apparatus 200 may be designed to include one or more rigid portions in addition to the rigid portion 202. The additional rigid portions may include one or more apertures. For example, the adaptive surface surgical guiding apparatus 200 may include one or more apertures in the rigid portion 202 and/or the variable deformable portion 204. The apertures may include a drill hole, a cut slot, and the like, for allowing a physician to operate surgical tools through the apertures. In some embodiments, two apertures may be placed in two different regions of the variable deformable portion 204, and those apertures may correspond to two regions of the femur 212 for which surgery is to take place. The apertures may be rigid enough so that a physician can accurately drill a hole into femur 212 through the apertures without any movement of the apertures relative to femur 212. Specific examples of apertures will be discussed in more detail below with respect to FIGS. 4a and 4b.

Figure 3A:
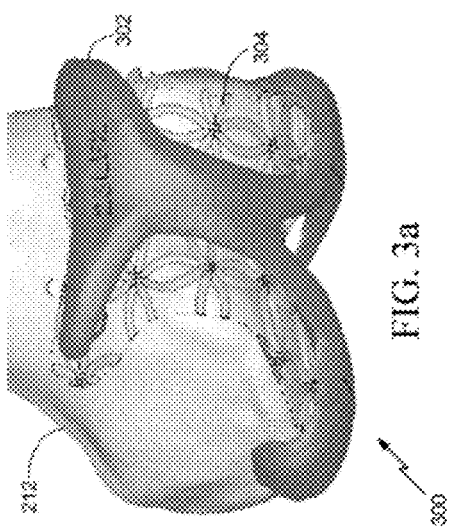
FIG. 3*a* illustrates an anterior perspective view of an example of a surgical guiding apparatus in accordance with some embodiments.
Figure 3B:
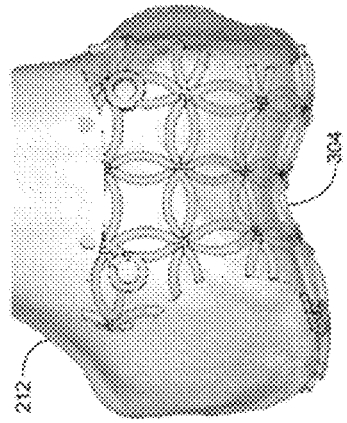
FIG. 3*b* illustrates an anterior view of an example of a variable deformable portion of the surgical guiding apparatus of FIG. 3*a* in accordance with some embodiments.
Figure 3C:
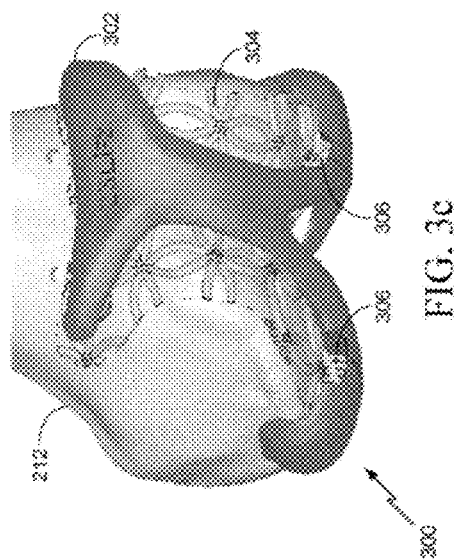
FIG. 3*c* illustrates an anterior perspective view of another example of a surgical guiding apparatus in accordance with some embodiments.
Figure 3D:
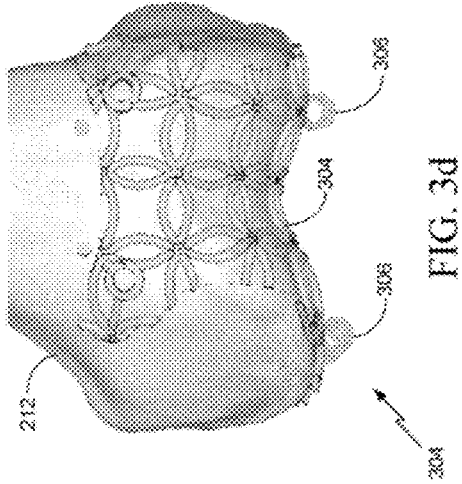
FIG. 3*d* illustrates an anterior view of an example of a variable deformable portion of the surgical guiding apparatus of FIG. 3*c* in accordance with some embodiments.

FIGS. 3a-3d illustrate another example of an adaptive surface surgical guiding apparatus 300 including a variable deformable portion 304 and a rigid portion 302. The variable deformable portion 304 comprises a different pattern than that of the variable deformable portion 204 of the surgical guiding apparatus 200 illustrated in FIGS. 2a-2d. As such, the variable deformable portion 304 may be more flexible than the variable deformable portion 204 illustrated in FIGS. 2a-2d. FIGS. 3c and 3d additionally illustrate another example of a variable deformable portion 304 including two deformable linkages 306, which include springs that allow movement in an up and down direction.

Figure 4A:
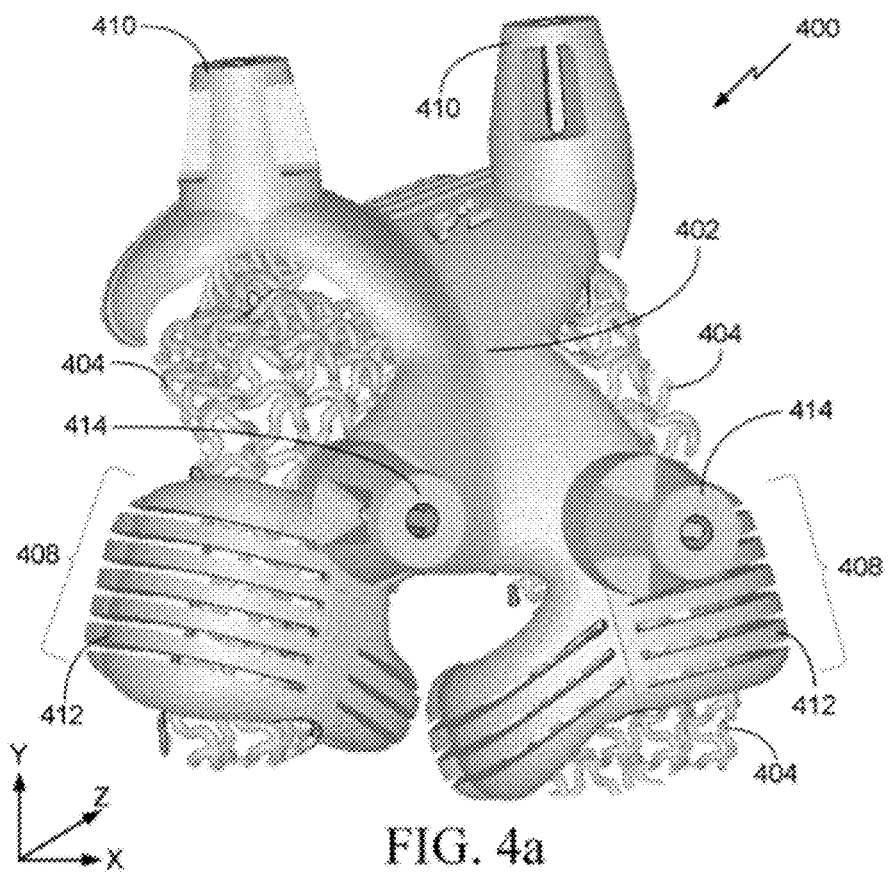
FIG. 4*a* illustrate a bottom view of another example of a surgical guiding apparatus in accordance with some embodiments.

FIG. 4a illustrates a bottom view of another example of an adaptive surface surgical guiding apparatus 400. The bottom view of FIG. 4a corresponds to bottom view A of the femur 100 illustrated in FIG. 1c.

The adaptive surface surgical guiding apparatus 400 includes an adaptive surface including a rigid portion 402, a variable deformable portion 404, and clamps 408. The rigid portion 402 and the variable deformable portion 404 may be similar to the rigid portion 202 and the variable deformable portion 204 described above with respect to FIGS. 2a-2d. The rigid portion 402 may be designed to attach to a well-defined region of an anatomical object (e.g. a bone) to provide a secure and stable attachment. For example, the rigid portion 402 may be attached to the anterior region of a femur such as femur 100 in FIG. 1c. The rigid portion 402 may be attached to the femur via the variable deformable portion 404. For example, the variable deformable portion 404 may be attached to the femur, and the rigid portion 402 may be attached to the variable deformable portion 404. The rigid portion 402 may be designed so as to not easily flex when an object comes into contact with the rigid portion 402 or when the rigid portion 402 makes contact with the surface of the femur. For example, the rigid portion 402 may be stable enough so that a physician can operate surgical tools (e.g. a drill) through part of the rigid portion 402 without movement of the rigid portion 402 relative to the femur.

In some embodiments, the rigid portion 402 may be fixedly attached to the femur. In other embodiments, the rigid portion 402 may be attached to the femur by resting on the femur. In these embodiments, clamps 408 may be used to secure the adaptive surface surgical guiding apparatus 400 to the femur. As described above, the well-defined regions of the femur upon which the rigid portion 402 is designed to attach may be clear in medical images and may be accurately modeled using the pre-operative and statistical methods described above for designing the adaptive surface surgical guiding apparatus 400.

The variable deformable portion 404 may be designed to conform to surfaces of the femur that are less well-defined and thus less accurately portrayed in the 3-D model of the femur. The variable deformable portion 404 may be designed so that it may be deformed in three-dimensions, including an X, Y, and Z direction or any combination thereof. As described above, the less well-defined regions may be less accurately portrayed in a 3-D model due to lack of detail in the corresponding medical images (e.g., due to soft-tissue), inaccuracies in the 3-D model, and the like. The flexible design of the variable deformable portion 404 allows the deformable portion 404 to attach to the underlying, variable anatomical surfaces to create a secure and stable fit and correct orientation for the surgical guiding apparatus 400. For example, the rigid portion 402 may attach to regions of the femur that are more accurately modeled in order to obtain the majority of the fit positioning of the adaptive surface surgical guide apparatus 400, and the variable deformable portion 404 may attach to the more variable, less-defined regions of the femur to achieve increased security and stability. In some embodiments, the variable deformable portion 404 may conform to the anterior region of the femur, as well as to the bottom region of the femur including the medial condyle 108 and the lateral condyle 110 (as illustrated in FIGS. 1a-d). The variable deformable portion 404 may be designed to conform to a large region of the anterior and bottom portions of the femur because there is more area in these regions that are less well-defined and/or more variable.

The deformability and/or flexibility of the variable deformable portion 404 may vary at different points of the variable deformable portion 404 based on the variability of the underlying surface of the femur, as described above, such that it can conform to variable surfaces and/or soft-tissue regions of the bone. The variable deformable portion 404 increases surface contact with the underlying surface of the femur, and thus can be used to increase stability of the adaptive surface surgical guiding apparatus 400 without the risk of creating a fulcrum point. In some embodiments, different material thicknesses and/or patterns may be used to vary the flexibility of the variable deformable portion 404, as described above.

The variable deformable portion 404 may be designed based on a best estimation of the expected underlying anatomical surface. For example, each point on the variable deformable surface 404 may be designed based on medical image data, statistical shape models, documented anatomical averages of anatomical objects, and/or one or more accuracy maps.

An estimated anatomical model of variable accuracy may be used as an initial design point for the variable deformable surface 404. Due to the inaccuracy and/or variability of the estimated model of the underlying anatomical surface, the variable deformable surface 404 may be designed with varying flexibility to conform to the anatomical surface. The use of estimated anatomical surfaces and accuracy maps is described in more detail above with respect to FIGS. 2a-2d, and applies equally to the design of the rigid portion 402 and the variable deformable portion 404.

The adaptive surface surgical guiding apparatus 400 further includes clamps 408. The clamps 408 include a group of deformable hinges 412. The deformable hinges 412 may be designed so that the clamps 408 may be deformed in only one dimension or direction, including an inward direction. The inward direction may be a combination of the X and Y directions. For example, the clamps 408 may be configured to attach to the medial condyle 108 and the lateral condyle 110 (as illustrated in FIG. 1). The deformable hinges 412 may only be deformed in an inward, one-dimensional direction toward and away from the corresponding condyle. The secure attachment of the clamps 408 to the condyles ensures that the adaptive surface surgical guiding apparatus 400 remains in a stable and secure position during surgery. The deformable hinges 412 may be designed to be flexible, and not rigid, because the condyles include soft-tissue that is not easily estimated in a model of the femur. Accordingly, the deformable hinges 412 allow the clamps 408 to attach to the condyles even in the absence of a well-defined model of the condyles. The deformable hinges 412 may be designed to be less flexible than the variable deformable portion 404, but more flexible than the rigid portion 402, based on the accuracy of the model of the femur. Additionally, one or more accuracy maps may be used to design the flexibility of the deformable hinges 412 using the techniques described above.

The adaptive surface surgical guiding apparatus 400 further includes apertures 410 and 414. The apertures 410 and 414 may be aligned with areas of the underlying femur surface that correspond to locations that need to be accessed for surgery, such as locations where holes are to be drilled. For example, the apertures 410 may be used for guiding a surgical device, such as a drill, to create holes 104 and 106 located on the anterior portion of the femur 100 (as illustrated in FIG. 1). Apertures 410 and 414 may additionally be designed to guide other surgical devices, such as: a drill, bur saw, jig saw, lateral drill, or any other cutting, milling, or drilling instrument.

Figure 4B:
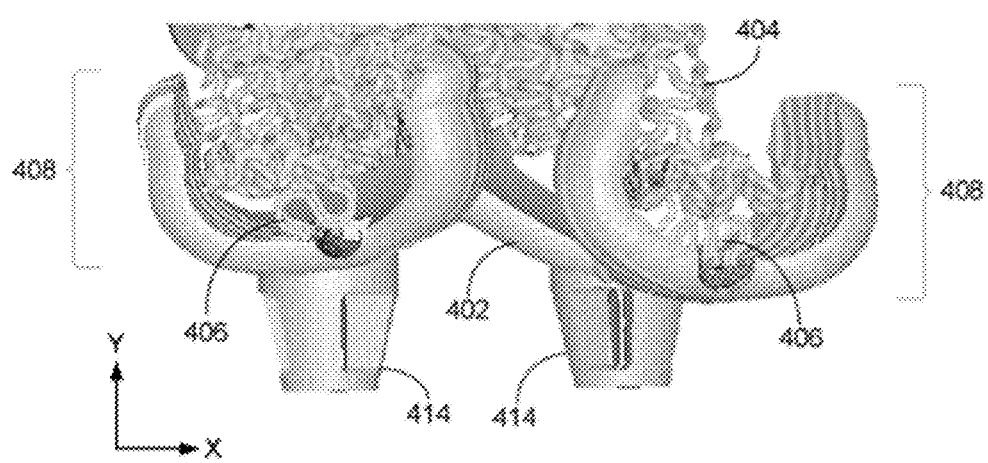
FIG. 4*b* illustrates a posterior view of the surgical guiding apparatus of FIG. 4*a* in accordance with some embodiments.

The apertures 410 and 414 are positioned so that a surgical device that is passed through one or more of the apertures 410 and 414 can reach the bone at the desired location. The apertures 410 and 414 may be positioned in any direction or angle relative to the bone as long as they provides access for a surgical device to reach the bone at the desired location. In some embodiments, the apertures 410 and 414 may protrude from the surface of the adaptive surface surgical guiding apparatus 400, as illustrated in FIGS. 4a and 4b. In other embodiments, the apertures 410 and 414 may be flush with the surface of the adaptive surface surgical guiding apparatus 400.

In some embodiments, the apertures 410 and 414 may include safety stops to prevent a surgical device from advancing beyond a planned or determined depth into the bone. While the description herein may describe apertures 410 and 414 with respect to specific locations on a femur, it will be apparent to one of skill in the art that the content of this disclosure applies equally to aperture locations relating to patient-specific locations on different type of bones, which be determined using pre-operative planning and procedures as described above.

FIG. 4b illustrates a posterior view of the adaptive surface surgical guiding apparatus 400 of FIG. 4a. The posterior view of FIG. 4b corresponds to the posterior view of the femur 100 illustrated in FIG. 1b. As illustrated in FIG. 4b, the variable deformable portion 404 may be coupled to the clamps 408 using deformable linkages 406. The deformable linkages 406 may be designed to be flexible in one or more dimensions. For example, the deformable linkages 406 may be flexible in the X and Y dimensions. In some embodiments, the deformable linkages 406 may include a spring, a flexible clip, a flexible hinge, a flexible clamp, or any other flexible linkage that allows movement or adaptability in one or more dimensions. One of skill in the art will understand that the deformable linkages may include any flexible linkage that allows movement or adaptability in one or more dimensions. In the embodiment illustrated in FIG. 4b, the deformable linkages 406 are designed to deform in an up and down direction (Y dimension) toward and away from the clamps 408 and in a left and right direction (X dimension) so that the adaptive surface surgical guiding apparatus 400 can adaptively fit to a variable underlying surface of the femur. One or more accuracy maps may be used to design the flexibility of the deformable linkages 406 using the techniques described above.

The rigid portion 402, the variable deformable portion 404, and the deformable hinges 412 of the clamps 408 are designed to provide an adaptive surface with varying flexibilities in different dimensions. The adaptive surface is based on the estimated accuracy of the underlying anatomical structure in order to create a secure and stable fit for the adaptive surface surgical guiding apparatus 400.

Figure 5A:
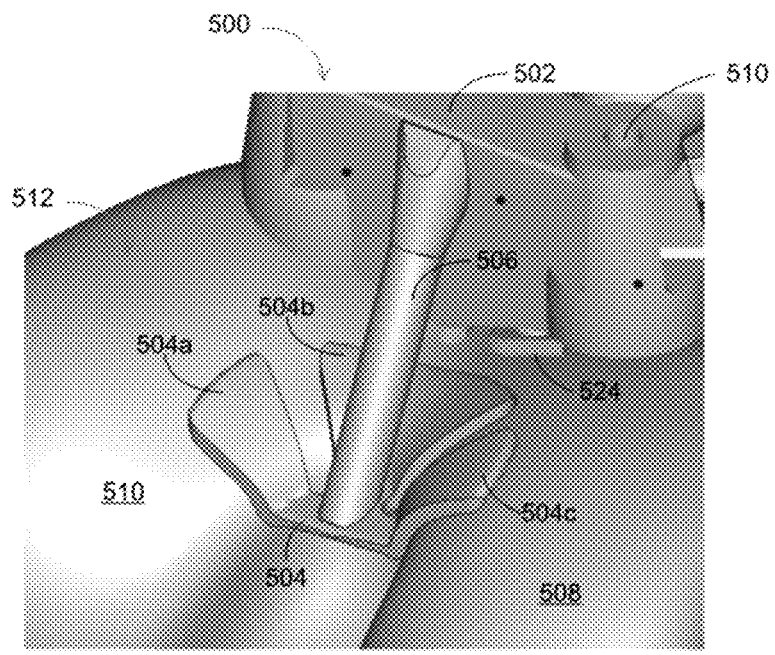
FIG. 5a illustrates a view of a variable deformable portion of a surgical guiding apparatus in accordance with some embodiments.

FIG. 5a illustrates a view of another embodiment of an adaptive surface surgical guiding apparatus 500. In the embodiment illustrated in FIG. 5a, the adaptive surface surgical guiding apparatus 500 is designed to attach securely and stably to femur 512. Adaptive surface surgical guiding apparatus 500 includes a first rigid portion 502, which includes an integral aperture 510. The first rigid portion 502 is attached to rigid linkage 506. In this embodiment, rigid linkage 506, unlike the previously described deformable linkages, is designed to be rigid and to restrict movement in all dimensions. However, in other embodiments, rigid linkage 506 could instead be replaced by a deformable linkage. Rigid linkage 506 is further attached to first variable deformable portion 504 and serves to link first variable deformable portion 504 with first rigid portion 502 in a rigid manner.

In some embodiments, rigid linkage 506 may be removable from rigid portion 502. For example, in the event that the fit with intracondylar notch 520 is found to be less than optimal during an operation, rigid linkage may be unattached from rigid portion 502 by, for example, sliding the shaft of rigid linkage 506 out from a complementary aperture (not shown) in rigid portion 502. In other embodiments, rigid linkage is integral with rigid portion 502.

Previously, the intracondylar notch (such as intracondylar notch 520) could be a difficult anatomical surface to use to increase surgical guide stability since the intracondylar notch surface is often covered by soft-tissue and the transition between cartilage and bone near that intracondylar notch is difficult to image and model using known techniques. As a result, it was difficult to design patient-specific surfaces accurate enough to create a secure and stable attachment between a portion of a surgical guide and the intracondylar notch surface. Thus, previous surgical guides may lack the ability to restrict all degrees of freedom and to create a secure and stable fit position of the guide. In particular, in cases where a bone (e.g. a femur) does not have any bony projections (e.g. osteophytes) to securely attach a surgical guide to, flexion may be a problem since the round or spherical shape of many bone parts (e.g. the condyles of a femur) may allow for rotational freedom of the surgical guide. An opposing force along the direction of rotation may help prevent rotation of a surgical guide. A variable deformable portion of a surgical guide that is designed to fit within an intracondylar notch may provide such an opposing force.

First variable deformable portion 504 is designed to fit within intracondylar notch 520 between lateral condyle 510 and medial condyle 508. In this embodiment, first variable deformable portion 504 includes three variable deformable members 504a-504c designed to interface with or attach to the intracondylar notch 520. The variable deformable members 504a-504c may vary in their flexibility from their base to their end by, for example, varying their thickness. In other embodiments, there may be more or fewer deformable members making up first variable deformable portion 504. Additionally, in this embodiment first variable deformable portion 504 includes variable deformable members 504a-504c that are patient-specific i.e. designed to interface more accurately with a particular patient's intracondylar notch 520. In other embodiments, the deformable members may not be patient-specific. In such instances, the deformable members may be made to be more flexible or deformable in order to accommodate more variability in a particular intracondylar notch.

The flexible surface of first variable deformable portion 504 allows adaptive surface surgical guide apparatus 500 to conform to the actual anatomic structures intra-operatively by compressing first variable deformable portion 504 as it is placed within the intracondylar notch 520. As first variable deformable portion 504 is compressed during placement, the adaptive surface surgical guide apparatus 500 aligns to the desired position within a range defined by the allowable deformation. Thus, the deformation of the first variable deformable portion 504 as it enters the intracondylar notch 520 provides additional stability by restricting degrees of freedom along the directions of deformation.

Figure 5B:
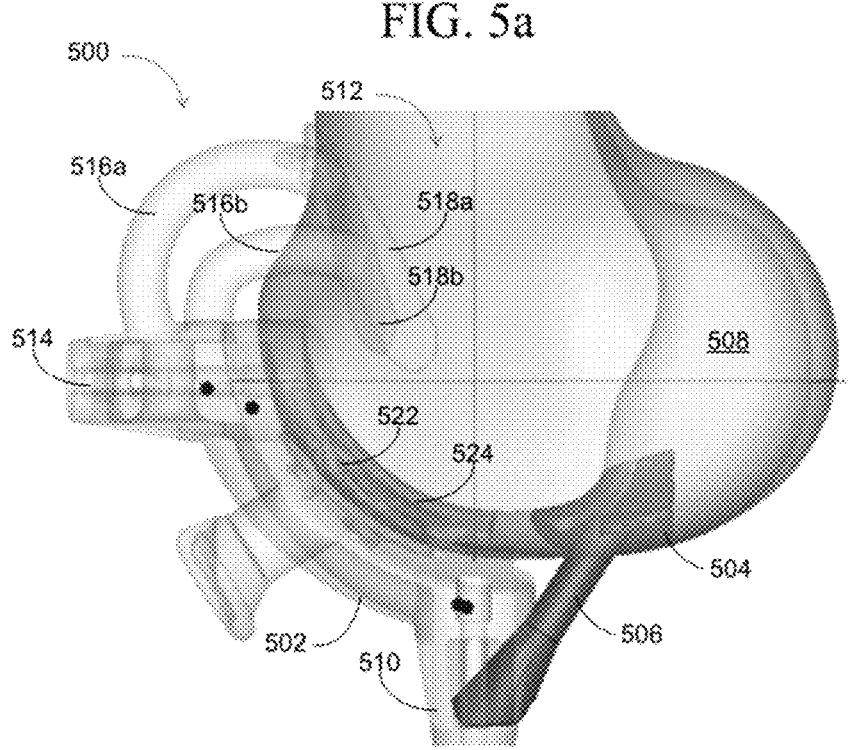
FIG. 5b illustrates a view of a surgical guiding apparatus in accordance with some embodiments.

FIG. 5b illustrates another, semi-transparent view of the adaptive surface surgical guide apparatus 500. Again, rigid linkage 506 is shown connected between first rigid portion 502 and first variable deformable portion 504. First variable deformable portion 504 is shown attached to intracondylar notch 520 (not shown). Apertures 510 and 514 are illustrated as integral with first rigid portion 502. Second rigid portions 516a and 516b are attached to first rigid portion 502. Second rigid portions 516a and 516b are further attached to second variable deformable portions 518a and 518b. Second variable deformable portions 518a and 518b attach to femur 512 to provide further security and stability to adaptive surface surgical guide apparatus 500. In other embodiments, second variable deformable portions 518a and 518b may instead be rigid portions. For example, where the model of femur 512 is very accurate in the interface area between femur 512 and elements 518a and 518b, a rigid portion may be used. Additionally, elements 518a and 518b, whether rigid or deformable, may be patient-specific.

Also attached to first rigid portion 502 are deformable members 522, which in this embodiment are springs. Deformable members 522 (i.e. springs) are attached to third variable deformable portion 524. Deformable members 522 allow third variable portion 524 to move relative to femur 512 while attaching adaptive surface surgical guide apparatus 500 to femur 512. Deformable members 522 may be of uniform deformability (e.g. spring rate) or may have varying deformabilities based on the confidence of the 3-D model at the underlying position of each deformable member. Additionally, the deformable members 522 may have variable deformabilities (i.e. spring rates) based on the amount of deformation or compression of each individual deformable member. For example, a particular deformable member may be very compliant (e.g. low spring rate) on first contact, but may increase in resistance (e.g. high spring rate) as the level of deformation or compression increases. Third variable deformable portion 524 attaches to femur 512 to provide further security and stability to adaptive surface surgical guide apparatus 500. As with before, third variable deformable portion 524 may optionally be rigid and/or patient-specific.

Figure 6A:
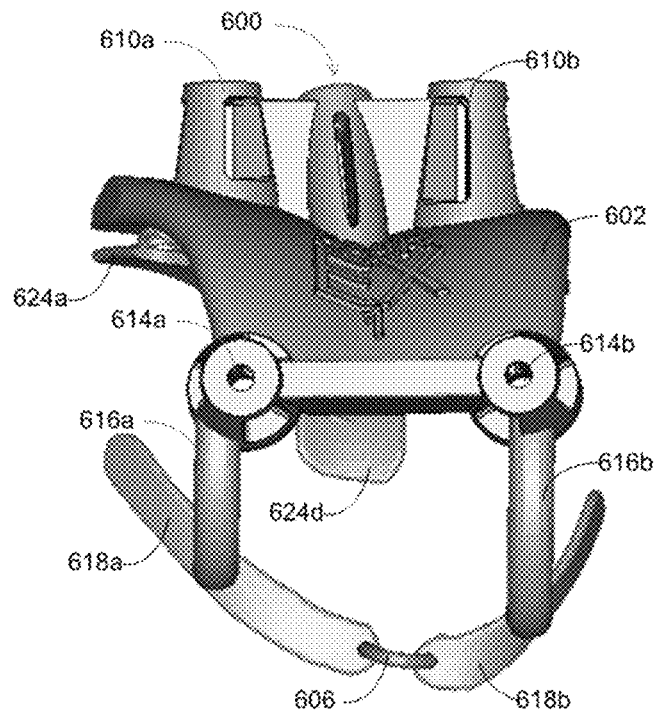
FIG. 6a illustrates a view of a surgical guiding apparatus in accordance with some embodiments.

FIG. 6a illustrates a view of another embodiment of an adaptive surface surgical guiding apparatus 600. In the embodiment illustrated in FIG. 6a, the adaptive surface surgical guiding apparatus 600 is designed to attach securely and stably to a femur (not shown). Those of skill in the art will appreciate that similar designs may be used to attach to different types of bones.

Adaptive surface surgical guiding apparatus 600 includes a first rigid portion 602 (i.e. a body) and apertures 610a-b and 614a-b attached thereto, which may be used, for example, for guiding surgical devices (e.g. a drill). Second rigid portions 616a and 616b are also attached to first rigid portion 602. Here, second rigid portions 616a and 616b take the form of rigid arms extending from first rigid portion 602. However, in other embodiments second rigid portions 616a and 616b may be formed in different shapes. Second rigid portions 616a and 616b are further attached to second variable deformable portions 618a and 618b. In some embodiments, second rigid portions 616a and 616b include stiffening flanges (not shown), connected between the second rigid portions 616a and 616b and the second variable deformable portions 618a and 618b. In such embodiments, the stiffening flanges stiffen the connection (i.e. make it less deformable) between the second rigid portions 616a and 616b and the respective second variable deformable portions 618a and 618b. It will be appreciated by those of skill in the art that stiffening flanges may also be used to stiffen the connection between other aspects of adaptive surface surgical guiding apparatuses.

Second variable deformable portions 618a and 618b attach to a bone to provide further security and stability to adaptive surface surgical guide apparatus 600. In some embodiments, second variable deformable portions 618a and 618b may be designed to attach to anterior portions of a femur (including the shaft of the femur) and so may be referred to as anterior support elements. In other embodiments, second variable deformable portions 618a and 618b may instead be rigid portions. For example, where the model of an underlying bone (e.g. a femur) is very accurate in the interface area between the bone and elements 618a and 618b, a rigid portion may be used instead. Additionally, elements 618a and 618b, whether rigid or deformable, may be patient-specific i.e. shaped to conform to a patient's specific anatomical features.

Second rigid portions 616a and 616b are connected by a deformable linkage 606. Deformable linkage 606 may include a spring, a flexible clip, a flexible hinge, a flexible clamp, or any other flexible linkage that allows movement or adaptability in one or more directions. In this embodiment, deformable linkage is a flexible buckle that allows second variable deformable portions 618a and 618b to move relative to each other while adaptive surface surgical guide apparatus 600 is being attached to a bone surface. However, deformable linkage 606 constrains the overall movement of second variable deformable portions 618a and 618b so that, for example, the variable deformable portions are not deformed too significantly, which may cause misalignment of adaptive surface surgical guide apparatus 600.

Figure 6B:
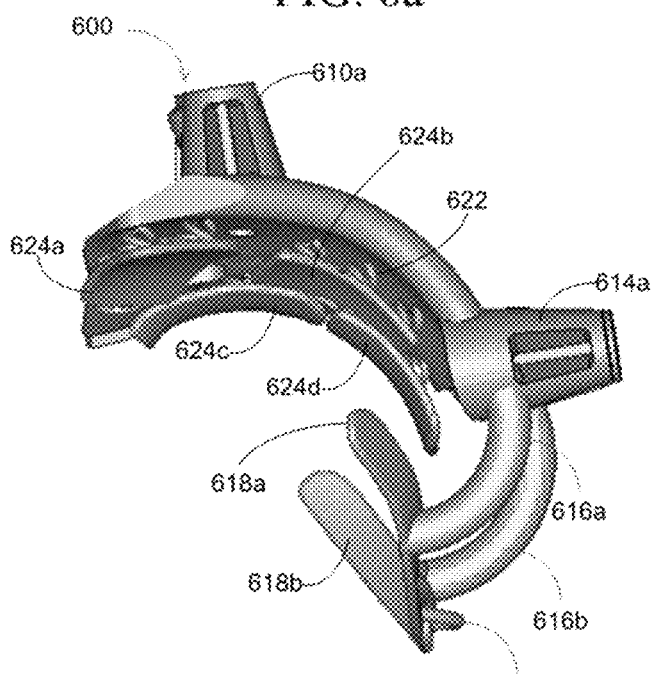
FIG. 6b illustrates a view of a surgical guiding apparatus in accordance with some embodiments.

As shown in FIG. 6b, also attached to first rigid portion 602 are deformable members 622, which in this embodiment are springs. Deformable members 622 are attached to third first deformable portions 624a-624d. In this embodiment, first variable deformable portions 624a-624d may also be referred to as distal support elements. Deformable members 622 allow third variable portions 624a-624d to move relative to a bone (e.g. a femur) while attaching adaptive surface surgical guide apparatus 600 to the bone. As with above, deformable members 622 may be of uniform deformability (e.g. spring rate or compression rates) or may have varying deformabilities based on the confidence of the 3-D model at the underlying position of each deformable member. Additionally, the deformable members 622 may have variable deformabilities based on the amount of deformation or compression of each individual deformable member. For example, a particular deformable member may be very compliant (e.g. compression rate) on first contact, but may increase in resistance (e.g. high compression rate) as the level of deformation or compression increases.

Deformable members 622 are attached to first variable deformable portions 624a-624d, which are designed to attach to a bone (e.g. a femur) to provide further security and stability to adaptive surface surgical guide apparatus 600. As with before, first variable deformable portions 624a-624d may optionally be rigid and/or patient-specific. First variable deformable portions 624a-624d may be spaced apart (as shown) in order to account for patient-specific anatomical features on the underlying bone, such as soft-tissues or other bony masses. The particular spacing and arrangement of first variable deformable portions 624a-624d may be pre-operatively designed based on a 3-D or other model of the underlying bone with which they are meant to attach. In other embodiments, first variable deformable portions 624a-624d may instead be fewer in number, or even a single surface. In this embodiment, the broad base of first rigid portion 602 allows for many arrangements of the variable deformable members and their attached variable deformable portions.

Figure 7A:
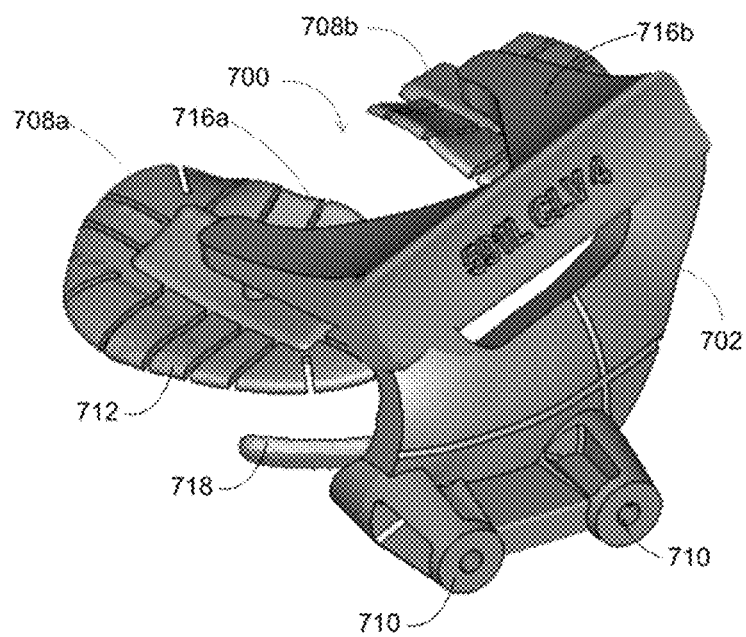
FIG. 7a illustrates a view of a surgical guiding apparatus in accordance with some embodiments.

FIG. 7a illustrates a view of another embodiment of an adaptive surface surgical guiding apparatus 700. In the embodiment illustrated in FIG. 7a, the adaptive surface surgical guiding apparatus 700 is designed to attach securely and stably to a tibia (not shown). Those of skill in the art will appreciate that similar designs may be used to attach to different types of bones.

Adaptive surface surgical guiding apparatus 700 includes a first rigid portion 702 (i.e. a body) and apertures 710 attached thereto, which may be used, for example, for guiding surgical devices (e.g. a drill). Second rigid portions 716a and 716b are also attached to first rigid portion 702. Here, second rigid portions 716a and 716b are integral with rigid portion 702. However, in other embodiments second rigid portions 716a and 716b may be formed in different shapes (e.g. arms as described above). Second rigid portions 716a and 716b are further attached to first variable deformable portions 708a and 708b.

First variable deformable portions 708a and 708b include deformable hinges 712. Together, first variable deformable portions 708a and 708b and deformable hinges 712 attach to a bone to provide further security and stability to adaptive surface surgical guide apparatus 700. In some embodiments, the deformable hinges are thinner than their respective first variable deformable portions. In such embodiments, the purpose of the deformable hinges is not so much to provide stability to the adaptive surface surgical guide apparatus 700, but to provide visual feedback to a user, such as a doctor, who is attaching the guide.

In some embodiments, first variable deformable portions 708a and 708b may be designed to attach to proximal portions of a tibia (including the tibial plateaus) and so may be referred to as proximal support elements. In such embodiments, first variable deformable portions 708*a* and 708*b* may have distinct shapes that reflect the distinct shapes of the bone portions they are intended to attach to. Alternatively, first variable deformable portions 708*a* and 708*b* may have standard shapes that may be replaceable (i.e. attached or unattached from second rigid portions 716*a* and 716*b*). In such cases, a user may select an appropriate shape of first variable deformable portion intra-operatively. In other embodiments, first variable deformable portions 708*a* and 708*b* may instead be rigid portions. For example, where the model of an underlying bone (e.g. a tibia) is very accurate in the interface area between the bone and elements 708*a* and 708*b*, a rigid portion may be used instead. Additionally, elements 708*a* and 708*b*, whether rigid or deformable, may be patient-specific i.e. shaped to conform to a patient's specific anatomical features.

A second variable deformable portion 718 is also connected to rigid portion 702 of adaptive surface surgical guiding apparatus 700. In this embodiment, the second variable deformable portion is designed to attach to an anterior portion of a tibia and so may be referred to as an anterior support element. In other embodiments, second variable deformable portion 718 may instead be rigid. Additionally, variable deformable portion 718, whether rigid or deformable, may be patient-specific.

Figure 7B:
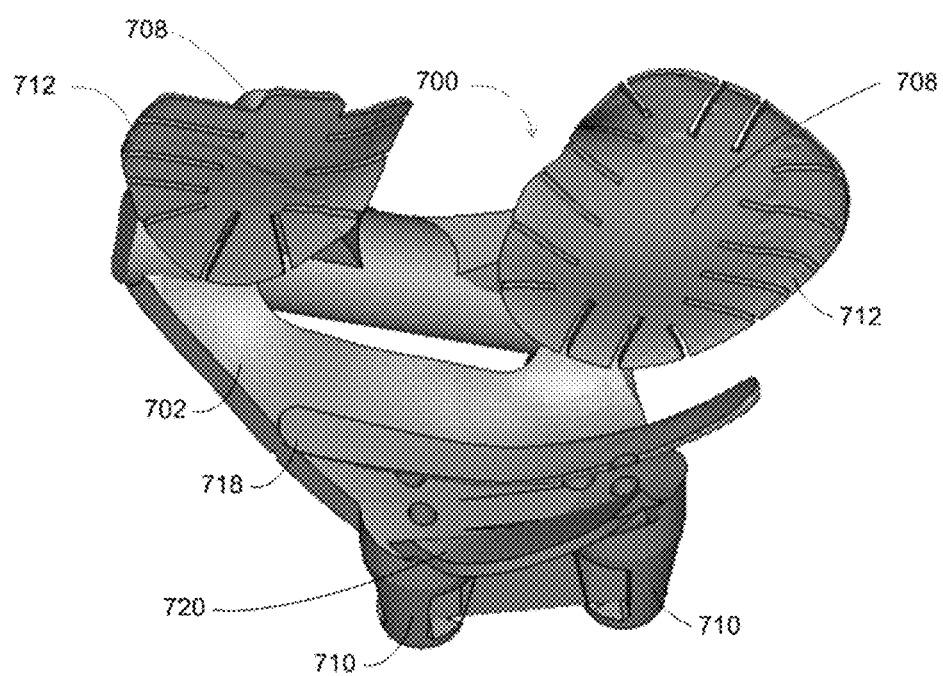
FIG. 7b illustrates a view of a surgical guiding apparatus in accordance with some embodiments.

As shown in FIG. 7*b*, also attached to first rigid portion 702 is a third rigid portion 720. In this embodiment, the third rigid portion 720 is designed to attach to an anterior portion of a tibia and may be referred to as an anterior lip. In other embodiments, third rigid portion 720 may instead be deformable. Additionally, third rigid portion 720, whether rigid or deformable, may be patient-specific.

Figure 8A:
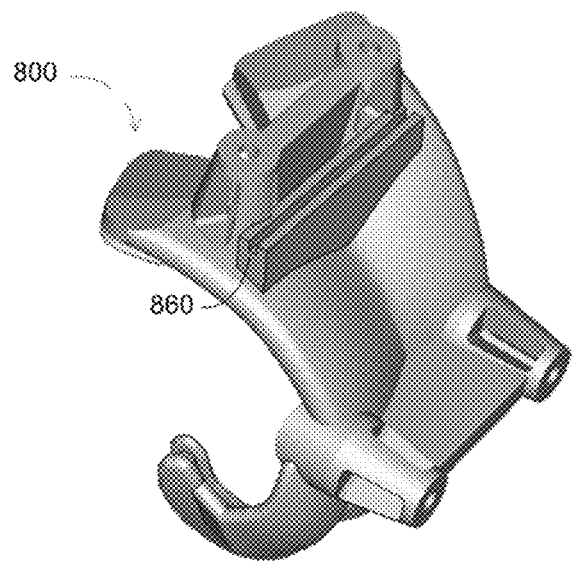
FIG. 8a illustrates a view of another embodiment of an adaptive surface surgical guiding apparatus 800 including an accessory slot.

FIG. 8*a* illustrates a view of another embodiment of an adaptive surface surgical guiding apparatus 800. The adaptive surface surgical guiding apparatus 800 illustrated in FIG. 8 is similar to the embodiment described with respect to FIGS. 6*a*-6*b*, so like features will not be described again. In the embodiment illustrated in FIG. 8*a*, the adaptive surface surgical guiding apparatus 800 includes an accessory slot 860.

Accessory slot 860 can be used to attach various tools to adaptive surface surgical guiding apparatus 800. These attachable tools may be patient-specific or standard off-the-shelf items.

Figure 8B:
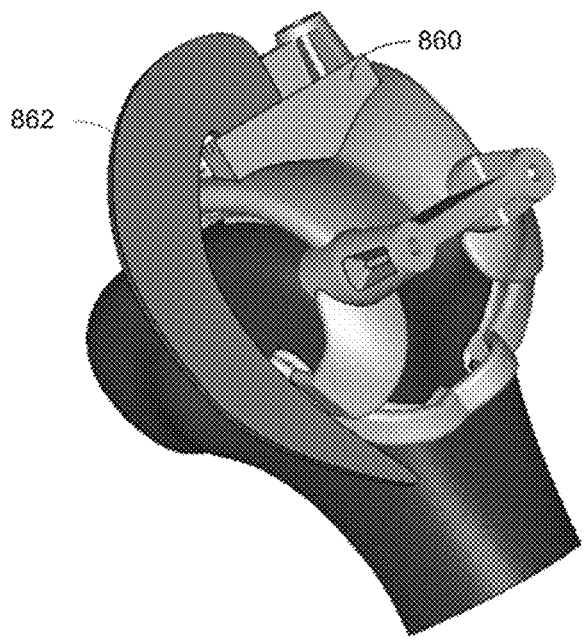
FIG. 8b illustrates a view of an embodiment of an adaptive surface surgical guiding apparatus 800 including a resection guide installed in an accessory slot.

For example, accessory slot 860 may be configured to receive a verification element such as resection guide 862 shown in FIG. 8*b*. In some embodiments, the resection guide 862 may be referred to as an "angel wing" as known by skilled artisans. The resection guide may be used before making a resection or osteotomy to verify the location of the cutting plane with respect to an anatomical object, such as a bone. For example, in a total knee arthroplasty, a resection guide such as guide 862 may be used for an anterior femoral cut to prevent notching.

Embodiments of resection guides may take many shapes as dictated by a patient's anatomy, the surgical plan, and other considerations as known by those of skill in the art. In addition, other types of verification elements, as are known by those of skill in the art, may be attached to adaptive surface surgical guiding apparatus 800 using accessory slot 860.

As discussed above, achieving greater stability of surgical guiding apparatuses may be facilitated by increasing the number and/or size of support surfaces attached to an anatomical object (such as a bone). In previously described embodiments, a combination of rigid and deformable portions serve to place support surfaces (including patient-specific surfaces) in contact with the anatomical object. Unfortunately, it is not always possible to achieve sufficient security and stability of a surgical guide without removing soft-tissue(s) (e.g. cartilage) from the anatomical object. But removing additional soft-tissue is generally undesirable.

Accordingly, in some embodiments, one or more soft-tissue piercing pins may be used to pierce soft-tissue (such as cartilage, tendons, etc.) attached to an anatomical object (such as a bone) in order to increase surgical guide stability. Additionally, such soft-tissue piercing pins may be used to verify the correctness of the fit of a surgical guide. In order to avoid contamination and infection, the soft-tissue piercing pin may be designed to be a feature of a surgical guide such that the pin only pierces soft-tissue within an area of an incision, but does not pierce the skin outside of the surgical site (e.g. the dermis and epidermis).

In some embodiments, the soft-tissue piercing pin may be an integral part of a surgical guide. In such embodiments, the design of the surgical guide should be such that, upon normal attachment of the surgical guide to an anatomical object (such as a bone), the pin enters the soft-tissue in the correct location and does not pierce the skin. Once attached, the soft-tissue piercing pin acts as a support surface that attaches to the anatomical object through intervening soft-tissue, which increases the security and stability of the attached surgical guide.

In other embodiments, the soft-tissue piercing pin can be an optional i.e. removable accessory to the surgical guide. For example, if it is not possible to design the surgical guide so that the trajectory of the soft-tissue piercing pin through the soft-tissue upon normal placement of the guide leads the pin to the correct position, the surgical guide may include a pin-guiding aperture. In such embodiments, after placement of the surgical guide, the soft-tissue piercing pin may be manually inserted through the aperture, piercing the soft-tissue until it hits an anatomical object (such as a bone). In such embodiments, the surgical guide and soft-tissue piercing pin may include markings so that the soft-tissue piercing pin can act as a depth gauge. When used in this manner, the soft-tissue piercing pin functions as a means of verifying the correctness of the fit of the surgical guide to the anatomical object.

In further embodiments, the soft-tissue piercing pin may be an integral part of an attachment component, including "off-the-shelf" components, which can be connected to the surgical guide either before or after placing the guide on the bone.

Figure 9:
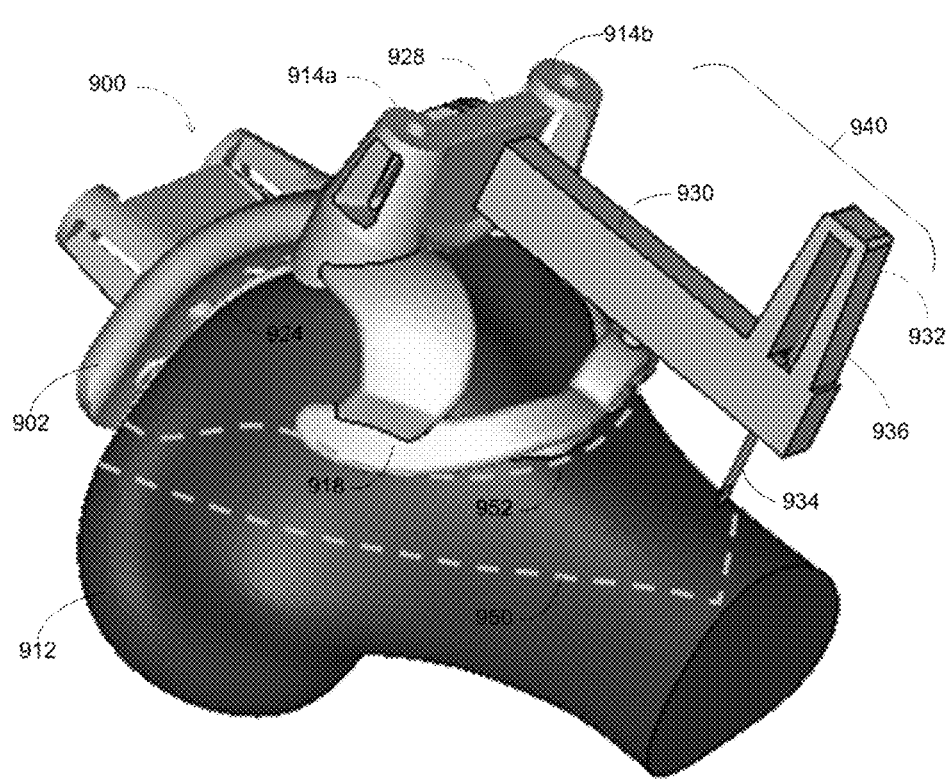
FIG. 9 illustrates an embodiment of an adaptive surface surgical guiding apparatus including a soft-tissue piercing pin.

FIG. 9 illustrates an embodiment of an adaptive surface surgical guiding apparatus 900 including a soft-tissue piercing pin 934. The soft-tissue piercing pin 934 is a type of stability element i.e. an element designed to stabilize the attachment of adaptive surface surgical guiding apparatus 900 to an underlying anatomical object. The adaptive surface surgical guiding apparatus 900 illustrated in FIG. 9 is similar to the embodiment described with respect to FIGS. 6*a* and 6*b*, so like features will not be described again.

In FIG. 9, broken line 950 indicates a line of incision whereby the skin is split to reveal an area of operation. The area between broken line 950 and broken line 952 represents a soft-tissue area where soft-tissue (not shown) overlies femur 912. Similar to the embodiments described with reference to FIGS. 6*a* and 6*b*, various stability elements of adaptive surface surgical guiding apparatus 900, such as deformable portions 918 and 924, attach to surfaces of femur 912 that are mostly devoid of soft-tissue. But in order to provide additional stability elements outside of these surfaces, using the deformable elements such as those described above, additional soft-tissue may have to be removed. Rather than remove additional soft-tissue, a soft-tissue piercing pin 934 may be used to provide an additional attachment to femur 912, thereby providing additional security and stability to adaptive surface surgical guiding apparatus 900 when fitted.

In the embodiment depicted in FIG. 9, adaptive surface surgical guiding apparatus 900 includes third rigid portion 930, which is affixed to rigid support member 928. Rigid support member 928 is integral on each side with apertures 914a and 914b and with first rigid portion 902. In this embodiment, third rigid portion 930 is permanently affixed and therefore integral with adaptive surface surgical guiding apparatus 900. However, in other embodiments, third rigid portion 930 may be part of a removable soft-tissue piercing pin attachment 940. Additionally, third rigid portion 930 may be attached to other aspects of adaptive surface surgical guiding apparatus 900.

Third rigid portion 930 includes member 932. Member 932 may include an aperture (not shown) through which soft-tissue piercing pin 934 is inserted. In such embodiments, member 932 may provide lateral support for the soft-tissue piercing pin 934. In embodiments where soft-tissue piercing pin 934 is not permanently affixed to third rigid portion 934, but is moveable through an aperture in third rigid portion 934, and where member 932 has a recess 936 where soft-tissue piercing pin 934 may be seen, the movement of soft-tissue piercing pin 934 may act as a depth or fit indicator. For example, as adaptive surface surgical guiding apparatus 900 is attached to femur 912, soft-tissue piercing pin 934 will move up into the recess 936 in member 932 until it contacts the top of the recess 936. At such time, it may be determined that the adaptive surface surgical guiding apparatus 900 is in the correct position. In other embodiments, soft-tissue piercing pin 934 may be permanently or removably affixed to third rigid member 930 without member 932.

Member 932 may also be used as an appendage to help push the soft-tissue piercing pin 934 through soft-tissue (not shown). By providing a contact surface higher than rigid portion 930, member 932 may facilitate attachment of adaptive surface surgical guiding apparatus 900 by providing a surface above the level of the anatomical object.

In some embodiments, soft-tissue piercing pin 934 may be moveable and biased by a deformable member such as a spring. In such cases, member 932 may enclose a deformable biasing member (such as a spring, which is not shown) attached to the top of soft-tissue piercing pin 934. In such embodiments, soft-tissue piercing pin 934 may be biased such that the pin 934 pierces soft-tissue (such as cartilage) but not harder anatomical objects (such as bones) when adaptive surface surgical guiding apparatus 900 is fitted. Thus, the deformable biasing member (not shown) within member 932 may allow for some inaccuracy in the design of adaptive surface surgical guiding apparatus 900 because the soft-tissue piercing pin 934 can still attach to an underlying anatomical object even if the design of adaptive surface surgical guiding apparatus 900 is not exact.

Figure 10:
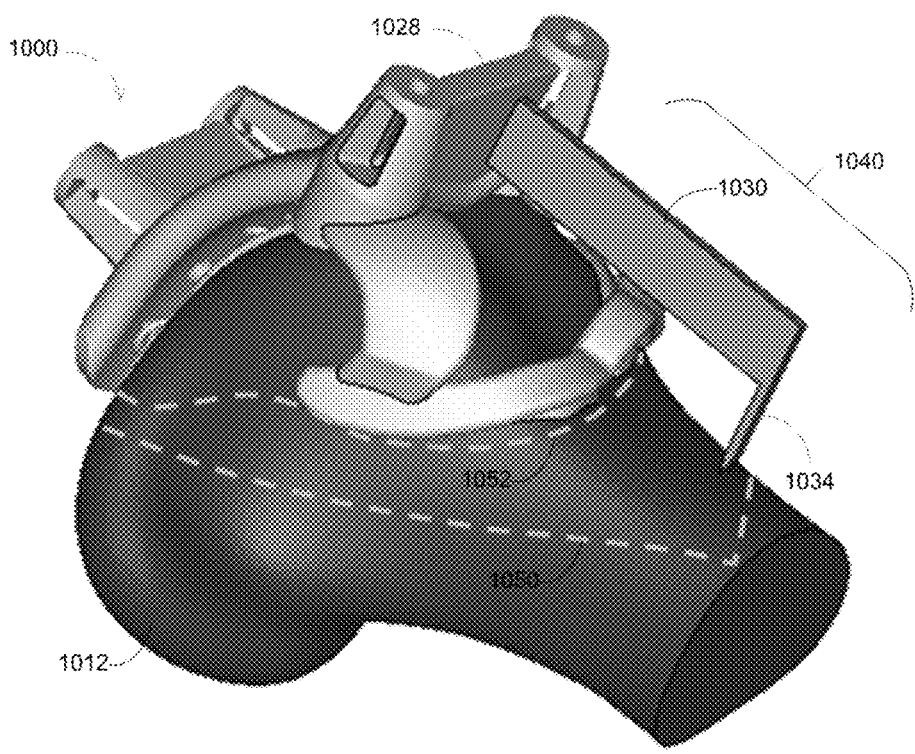
FIG. 10 illustrates another embodiment of an adaptive surface surgical guiding apparatus including a soft-tissue piercing pin.

FIG. 10 illustrates another embodiment of an adaptive surface surgical guiding apparatus 1000 including a soft-tissue piercing pin 1034. As with FIG. 8, the various support surfaces of adaptive surface surgical guiding apparatus 1000 attach to surfaces of femur 1012 that are mostly devoid of soft-tissue. And again, broken line 1050 indicates a line of incision whereby the skin is split to reveal an area of operation, and the area between broken line 1050 and broken line 1052 represents an area where soft-tissue (not shown) overlies femur 1012.

In the embodiment illustrated in FIG. 10, adaptive surface surgical guiding apparatus 1000 includes third rigid member 1030 and soft-tissue piercing pin 1034, which together comprise removable soft-tissue piercing pin attachment 1040. In this embodiment, soft-tissue piercing pin attachment 1040 is removably affixed to adaptive surface surgical guiding apparatus 1000. Also in this embodiment, soft-tissue piercing pin 1034 is integrally formed with third rigid member 1030 such that soft-tissue piercing pin attachment 1040 may be manufactured as a single piece.

Soft-tissue piercing pin attachment 1040 may be affixed to adaptive surface surgical guiding apparatus 1000 by a slot in rigid support member 1028 (not shown). However, in other embodiments, soft-tissue piercing pin attachment 1040 may be affixed to other aspects of adaptive surface surgical guiding apparatus 1000. In this way, one or more Soft-tissue piercing pin attachment (such as 1040) may be test fitted to an anatomical object (such as femur 1012) during an operation, and the best fit may be chosen accordingly. In this way, off-the-shelf or custom components may be made to work with adaptive surface surgical guiding apparatus 1000.

The different portions of the adaptive surface surgical guiding apparatuses described above are designed and manufactured to include varying deformabilities and flexibilities in order to create an adaptive surface for many bone types and locations. In some embodiments, one or more rigid portions are configured to overlap at least a part of one or more variable deformable portions. For example, a variable deformable portion may conform to a larger region of the anatomical surface than that upon which a rigid portion can attach because there is more area in these regions that are less well-defined and/or variable and that cannot be used to design the rigid portion for attachment thereto.

The combination of rigid portions and variable deformable portions described above provide a secure and stable attachment of the adaptive surface surgical guiding apparatuses to the underlying anatomy, even in regions that are highly variable and/or that are not well-defined in a 3-D model. Accordingly, an adaptive surface surgical guiding apparatus may be designed even using inexact representations and models of the underlying anatomy and despite the presence of highly variable anatomical surfaces.

In some embodiments of the adaptive surface surgical guiding apparatuses described above, the variable deformable portion or portions include a plurality of holes through which the underlying anatomical surface is exposed. In some embodiments, the plurality of holes are designed to add more deformability or flexibility to the variable deformable portion.

In some embodiments, one or more rigid portions are configured to overlap at least a part of a variable deformable portion. For example, the variable deformable portion may conform to a larger region of the anatomical surface than that upon which the rigid portion can attach because there is more area in these regions that are less well-defined and/or variable and that cannot be used to design the rigid portion for attachment thereto.

In some embodiments, a variable deformable portion is coupled to a rigid portion using at least one deformable linkage. In some embodiments, the at least one deformable linkage includes one or more springs. In other embodiments, the deformable linkages may include any of the deformable linkages described above.

In some embodiments, the adaptive surface surgical guiding apparatus design further includes at least one of a clip, a hinge, a clamp, and a spring coupled to at least one of a variable deformable portion and a rigid portion. For example, the surgical guiding apparatus may include a clamp, such as clamps 408. The clamp may include one or more a group of deformable hinges, such as deformable hinges 412, that are designed to be deformed in a particular direction.

In some embodiments, the underlying anatomical surface includes a femur, such as the femur 212. In these embodiments, a rigid portion is configured to attach to an anterior portion of the femur and one or more condyles of the femur, and a variable deformable portion is configured to conform to the shape of the anterior portion and the one or more condyles of the femur. In other embodiments, the underlying anatomical surface includes a tibia. In these embodiments, a rigid portion may be configured to attach to a proximal portion of the tibia, such as one or more tibial plateaus, and an anterior portion of the tibia.

Generally, the flexible or deformable portions of an adaptive surface surgical guide apparatus such those described above are designed to attach to regions of a bone where the model of the bone is less accurate. As such, the flexible or deformable portions of the adaptive surface surgical guide apparatus provide a way to get the guide in an approximate position. The rigid portions of an adaptive surface surgical guide apparatus, on the other hand, are designed to attach to regions of a bone where the model of the bone is more accurate. Thus, the rigid portions provide a hard stop for a final position of an adaptive surface surgical guide apparatus as it is being put into place.

In some embodiments, adaptive surface surgical guiding apparatuses may include only deformable portions of varying flexibilities. For example, a fully deformable or flexible guide may be designed, for example, for an anatomical surface that is not modeled or depicted accurately enough to use a rigid portion for attachment.

Figure 11:
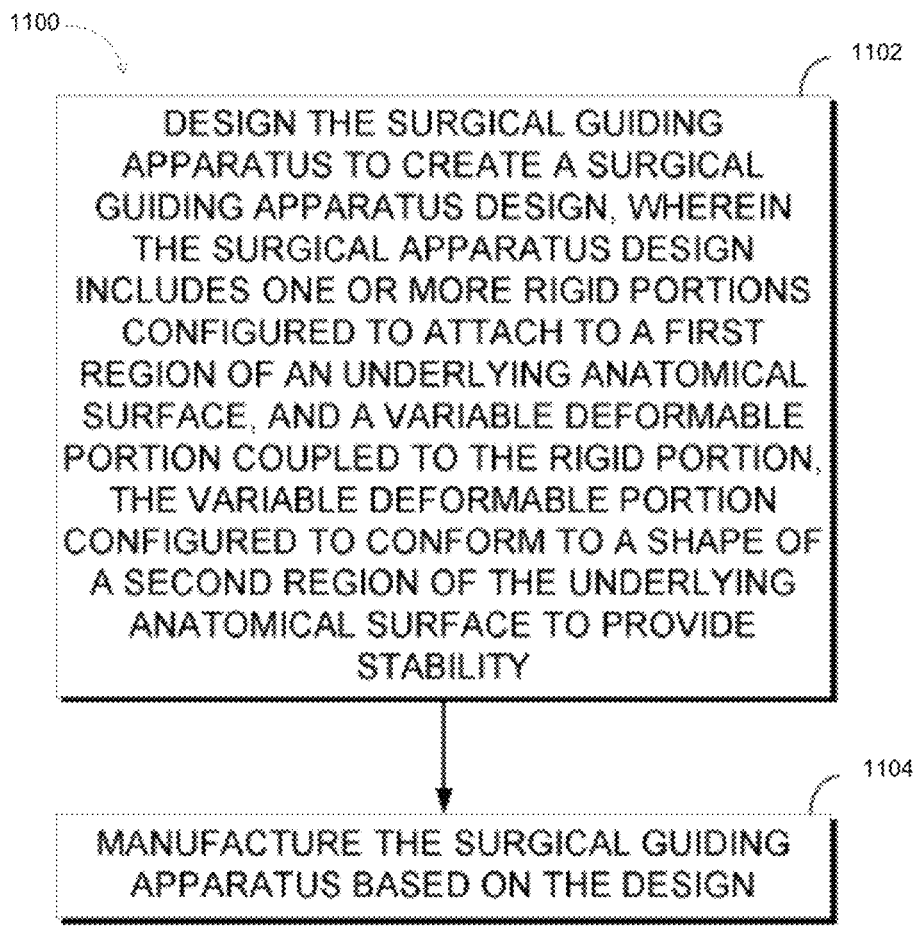
FIG. 11 illustrates an aspect of a method of manufacturing a surgical guiding apparatus.

FIG. 11 illustrates a method 1100 of manufacturing an adaptive surface surgical guiding apparatus. The method 1100 may be implemented to manufacture an adaptive surface surgical guiding apparatus such as, for example, adaptive surface surgical guiding apparatuses 200, 300, 400, 500, 600, 700, 800, 900 and/or 1000. Although the method 1100 may be described below with respect to elements of the adaptive surface surgical guiding apparatuses 200 and/or 400, those having ordinary skill in the art will appreciate that other components may be used to implement one or more of the blocks described herein.

At block 1102, the method begins with designing an adaptive surface surgical guiding apparatus to create an adaptive surface surgical guiding apparatus design. The adaptive surface surgical guiding apparatus design includes one or more rigid portions configured to attach to a first region of an underlying anatomical surface. For example, one or more rigid portions may include the rigid portions with reference to FIGS. 2-10. The adaptive surface surgical guiding apparatus design further includes one or more variable deformable portions coupled to the one or more rigid portions and configured to conform to a shape of a second region of the underlying anatomical surface in order to provide a secure and stable attachment of the adaptive surface surgical guiding apparatus to the underlying anatomical surface. For example, the one or more variable deformable portions may include any of the variable deformable portions described with reference to FIGS. 2-10.

In some embodiments, the method 1100 may further include the step of designing an accessory slot for the adaptive surface surgical guiding apparatus.

In some embodiments, the method 1100 may further include the step of designing a soft-tissue piercing element configured to pierce soft-tissue overlying a region of an underlying anatomical surface.

In some embodiments, the method 1100 may further include the step of designing the variable deformable portion to vary or flex different amounts at different points of the variable deformable portion based on an amount of variability of the underlying anatomical surface. For example, the deformability of the variable deformable portion may be designed to increase among the different points as the variability of the underlying anatomical surface for which the different points are configured to attach increases. For example, a large region of the anatomical surface may include soft-tissue that fails to show up in a medical image, such as an X-ray or a CT scan. The same or a different region of the anatomical surface may include a highly variable surface. The points on the variable deformable portion that are designed to attach to that region of the anatomical surface may be highly deformable or flexible so that those points can conform to the variable surface and/or the soft-tissue region of the anatomical surface. As described in more detail above, different material thicknesses and/or patterns may be used to vary the flexibility of the variable deformable portion.

In some embodiments, the method 1100 may further include the step of determining a range of variability of the underlying anatomical surface, and applying a variability map to the variable deformable portion based on the determined range of variability. The variability map specifies a deformability metric for a plurality of points of the variable deformable portion. For example, as described above, the deformability metric for a given point on the variability map corresponds to the variability of a corresponding point on the surface of the anatomical surface. The variability map may then be applied to the variable deformable portion so that each point of the variable deformable portion is designed to be deformable in proportion to the deformability metric of a corresponding point on the variability map. Based on the application of the variability map, points of the variable deformable portion that are designed to attach to highly inaccurately modeled and/or more variable regions of the underlying anatomical surface may be highly deformable so that the variable deformable portion will conform to the anatomical surface regardless of the variability of that surface.

At block 1104, the method 1100 concludes with manufacturing the adaptive surface surgical guiding apparatus based on the adaptive surface surgical guiding apparatus design. As described above, the surgical guiding apparatus may be designed according to patient-specific features of a patient's anatomy. The adaptive surface surgical guiding apparatus may be manufactured using additive manufacturing techniques, which are described in further detail below.

In some embodiments, the surgical guiding apparatuses 200, 300, 400, 500, 600, 700, 800, 900 and/or 1000 may be manufactured as a single, continuous structure (e.g., a single mold) that includes all of the adaptive surface guiding apparatus components, including: the rigid portion(s), the variable deformable portion(s), the deformable linkage(s), the clamp(s) (if present), and/or the aperture(s) (if present). In some embodiments, each component of the adaptive surface surgical guiding apparatuses 200, 300, 400, 500, 600, 700, 800, 900 and/or 1000 may be manufactured as a separate structure that is integrated with the other components to create the adaptive surface surgical guiding apparatuses.

In some embodiments, the adaptive surface surgical guiding apparatuses 200, 300, 400, 500, 600, 700, 800, 900 and/or 1000 may be partially or completely manufactured by additive manufacturing. Additive manufacturing or Rapid Prototyping and Manufacturing (RP&M) may be defined as a group of techniques used to fabricate an object using, for example, a 3-D computer aided design (CAD) of the object. Currently, a multitude of Rapid Prototyping techniques are available, including stereolithography (SLA), selective laser sintering (SLS), fused deposition modeling (FDM), foil-based techniques, and the like.

A common feature of additive manufacturing and RP&M techniques is that objects are typically built layer by layer. Stereolithography, for example, utilizes a vat of liquid photopolymer "resin" to build an object a layer at a time. On each layer, an electromagnetic ray traces a specific pattern on the surface of the liquid resin that is defined by the two-dimensional cross-sections of the object to be formed. The electromagnetic ray may be delivered as one or more laser beams which are computer-controlled. Exposure of the resin to the electromagnetic ray cures, or, solidifies the pattern traced by the electromagnetic ray, and causes it to adhere to the layer below. After a coat of resin has been had been polymerized, the platform descends by a single layer thickness and a subsequent layer pattern is traced, adhering the newly traced layer pattern to the previous layer. A complete 3-D object may be formed by repeating this process.

Selective laser sintering (SLS) is another additive manufacturing technique. SLS uses a high power laser or another focused heat source to sinter or weld small particles of plastic, metal, or ceramic powders into a mass that represents the 3-D object to be formed. SLS may be used to manufacture apparatuses requiring elastic or flexible materials. Materials used in the SLS process may include polyamide, polypropylene, and/or thermoplastic polyurethane. The different materials may be chosen for use in the SLS process based on the particular object or production method. For example, polypropylene may be used in a high-volume production of an object.

Fused deposition modeling (FDM) provides yet another additive manufacturing approach. FDM and other related techniques make use of a temporary transition from a solid material to a liquid state, usually due to heating. The material is driven through an extrusion nozzle in a controlled manner, and the material is then deposited a specified location. Details of one suitable FDM process are explained in U.S. Pat. No. 5,141,680, the entire disclosure of which is hereby incorporated by reference.

Foil-based techniques may also be used to support additive manufacturing. Foil-based techniques involve the use of glue or photo polymerization to fix coats of resin to each other. The desired object is then cut from these coats, or the object is polymerized from these coats.

Typically, additive manufacturing and RP&M techniques start from a digital representation of the 3-D object to be formed. Generally, the digital representation is sliced into a series of cross-sectional layers which are overlaid to form the object as a whole. Information about the cross-sectional layers of the 3-D object is stored as cross-sectional data. The RP&M system utilizes this cross-sectional data for the purpose of building the object on a layer-by-layer basis. The cross-sectional data used by the RP&M system may be generated using a computer system. The computer system may include software such as computer aided design and manufacturing (CAD/CAM) software to assist this process. Any suitable additive manufacturing technique known in the art may be used for converting the medical image information of the bone into a model, template, or mold that at least in part shows the positive or negative form of at least a portion of the bone. For example, a 3-D virtual model may be generated using medical image data, as described above, which may be used to generate an object using additive manufacturing techniques.

Using additive manufacturing obviates the need for assembly of different parts. Additive manufacturing also allows the integration of the various patient-specific components (e.g., the rigid portion, the variable deformable portion, the one or more clamps, the deformable linkages, the apertures, and the like), which further increases the accuracy of the adaptive surface surgical guiding apparatuses. The patient-specific components of the surgical guiding apparatuses may be designed based on patient-specific surfaces of a particular bone of a patient using, for example, the pre-operative procedures described above. The patient-specific components of the adaptive surface surgical guiding apparatuses may be made by generating portions that are complementary to the patient-specific parts of the bone.

The adaptive surface surgical guiding apparatuses described above (or parts thereof) may be manufactured using different materials. In some embodiments, only materials that are biocompatible (e.g. USP class VI compatible) with the human body are used. In some embodiments, an adaptive surface surgical guiding apparatus may be formed from a heat-tolerable material allowing it to tolerate high-temperature sterilization. In some embodiments, if SLS is used as a RP&M technique, the adaptive surface surgical guiding apparatus may be fabricated from a polyamide such as PA 2200 as supplied by EOS, Munich, Germany or any other material known by those skilled in the art may also be used.

Figure 12:
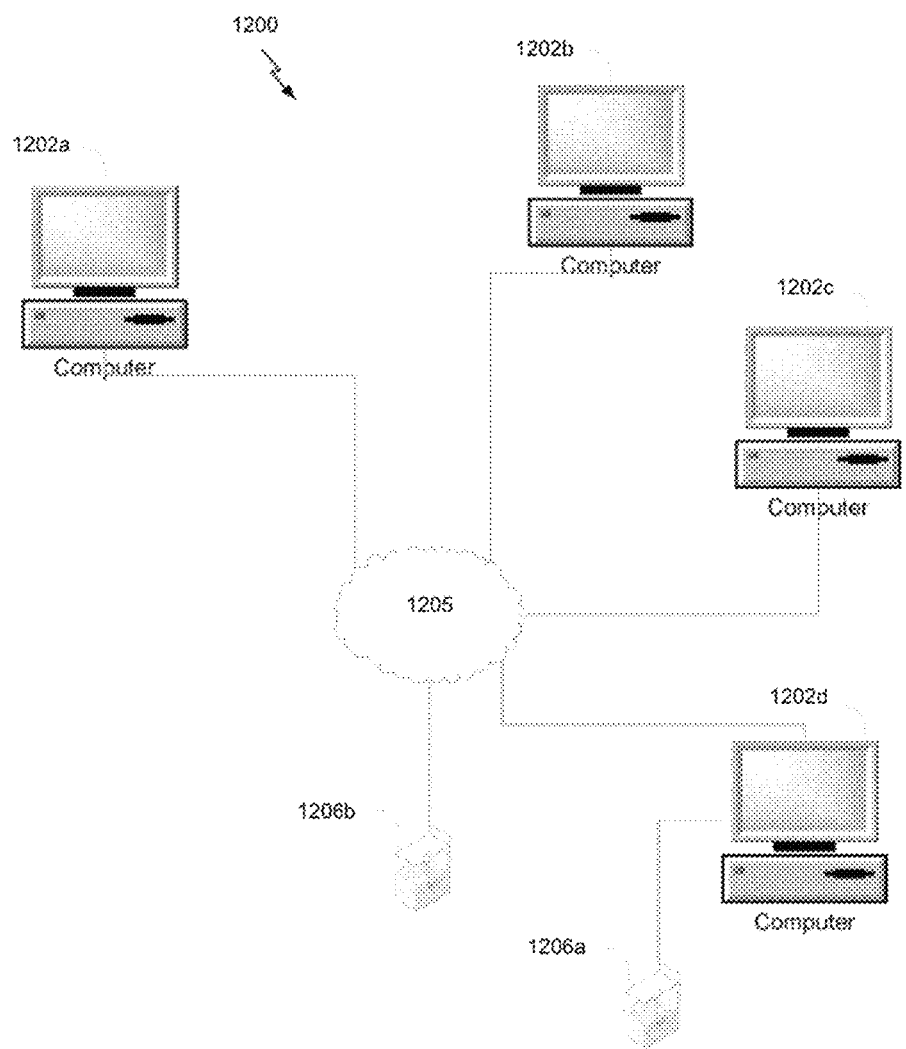
FIG. 12 is one example of a system for designing and manufacturing 3-D objects.

FIG. 12 illustrates one example of a system 1200 for designing and manufacturing 3-D devices and/or products. The system 1200 may be configured to support the techniques described herein. For example, the system 1200 may be configured to design and generate an adaptive surface surgical guiding apparatus, such as any one or more of those described above. In some embodiments, the system 1200 may include one or more computers 1202a-1202d. The computers 1202a-1202d may take various forms such as, for example, any workstation, server, or other computing device capable of processing information. The computers 1202a-1202d may be connected by a computer network 1205. The computer network 1205 may be the Internet, a local area network, a wide area network, or some other type of network. The computers may communicate over the computer network 1205 via any suitable communications technology or protocol. The computers 1202a-1202d may share data by transmitting and receiving information such as software, digital representations of 3-D objections, commands and/or instructions to operate an additive manufacturing device, and the like.

The system 1200 further may include one or more additive manufacturing devices 1206a and 1206b. These additive manufacturing devices may take the form of 3-D printers or some other manufacturing device as known in the art. In the example shown in FIG. 12, the additive manufacturing device 1206a is connected to the computer 1202a. The additive manufacturing device 1206a is also connected to computers 1202a-1202c via the network 1205 which connects computers 1202a-1202d. Additive manufacturing device 1206*b* is also connected to the computers 1202*a*-1202*d* via the network 1205. A skilled artisan will readily appreciate that an additive manufacturing device such as devices 1206*a* and 1206*b* may be directly connected to a computer 1202, connected to a computer 1202 via a network 1205, and/or connected to a computer 1202 via another computer 1202 and the network 1205.

Although a specific computer and network configuration is described in FIG. 12, a skilled artisan will also appreciate that the additive manufacturing techniques described herein may be implemented using a single computer configuration which controls and/or assists the additive manufacturing device 1206, without the need for a computer network.

Figure 13:
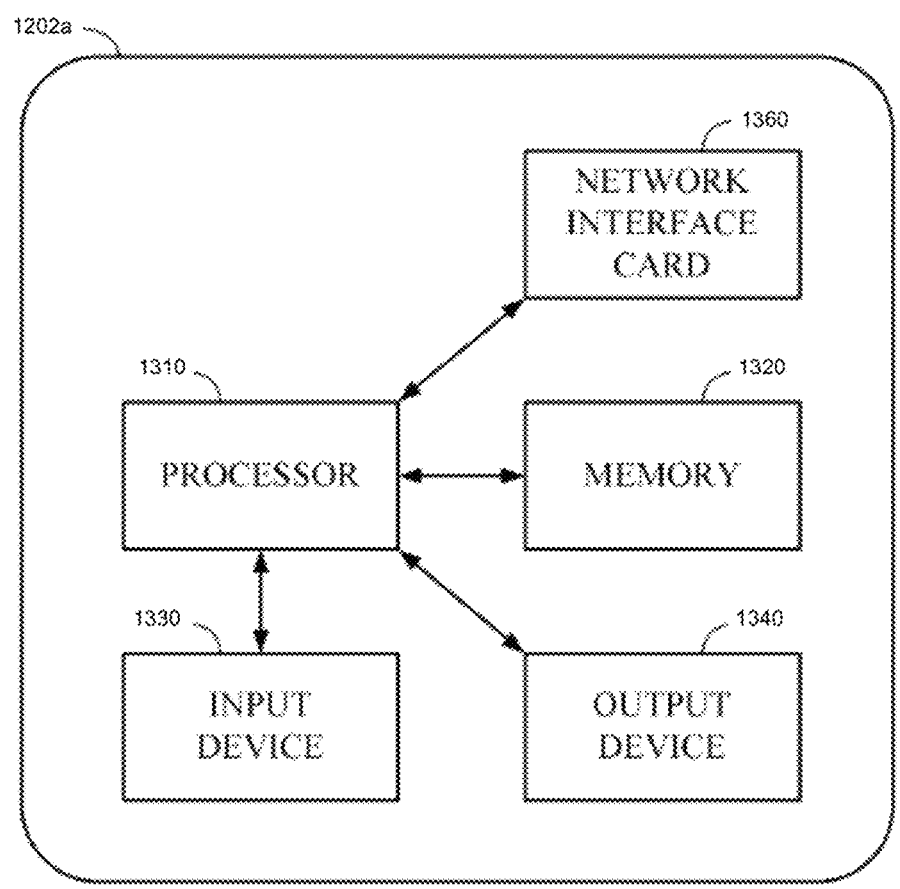
FIG. 13 is a functional block diagram of one example of a computer of FIG. 6.

FIG. 13 illustrates a more detailed view of computer 1202*a* illustrated in FIG. 9. The computer 1202*a* includes a processor 1310. The processor 1310 is in data communication with various computer components. These components may include a memory 1320, an input device 1330, and an output device 1340. In certain embodiments, the processor may also communicate with a network interface card 1360. Although described separately, it is to be appreciated that functional blocks described with respect to the computer 1202*a* need not be separate structural elements. For example, the processor 1310 and network interface card 1360 may be embodied in a single chip or board.

The processor 1310 may be a general purpose processor, a digital signal processor (DSP), an application specific integrated circuit (ASIC), a field programmable gate array (FPGA) or other programmable logic device, a discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 1310 may be coupled, via one or more buses, to read information from or write information to memory 1320. The processor may additionally, or in the alternative, contain memory, such as processor registers. The memory 1320 may include processor cache, including a multi-level hierarchical cache in which different levels have different capacities and access speeds. The memory 1320 may further include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 1310 may also be coupled to an input device 1330 and an output device 1340 for, respectively, receiving input from and providing output to a user of the computer 1202*a*. Suitable input devices include, but are not limited to, a keyboard, a rollerball, buttons, keys, switches, a pointing device, a mouse, a joystick, a remote control, an infrared detector, a voice recognition system, a bar code reader, a scanner, a video camera (possibly coupled with video processing software to, e.g., detect hand gestures or facial gestures), a motion detector, a microphone (possibly coupled to audio processing software to, e.g., detect voice commands), or other device capable of transmitting information from a user to a computer. The input device may also take the form of a touch-screen associated with the display, in which case a user responds to prompts on the display by touching the screen. The user may enter textual information through the input device such as the keyboard or the touch-screen. Suitable output devices include, but are not limited to, visual output devices, including displays and printers, audio output devices, including speakers, headphones, earphones, and alarms, additive manufacturing devices, and haptic output devices.

The processor 1310 further may be coupled to a network interface card 1360. The network interface card 1360 prepares data generated by the processor 1310 for transmission via a network according to one or more data transmission protocols. The network interface card 1360 may also be configured to decode data received via the network. In some embodiments, the network interface card 1360 may include a transmitter, receiver, or both. Depending on the specific embodiment, the transmitter and receiver can be a single integrated component, or they may be two separate components. The network interface card 1360, may be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein.

Figure 14:
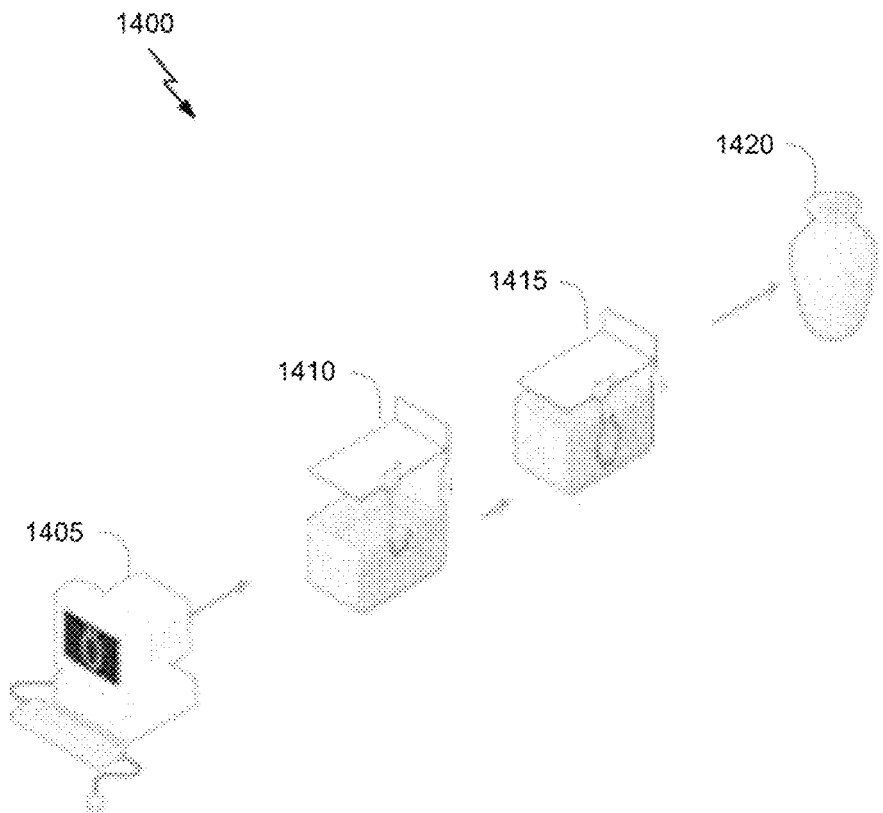
FIG. 14 is a process for manufacturing a 3-D object.

Using the devices described in connection with FIGS. 12 and 13, an additive manufacturing process may be employed to produce a 3-D product or device. FIG. 14 illustrates a general process 1400 for manufacturing an adaptive surface surgical guiding apparatus, such as those described above in connection with FIGS. 2-7.

The process begins at step 1405, where a digital representation of the device to be manufactured is designed using a computer, such as the computer 1202*a*. In some embodiments, a 2-D representation of the device may be used to create a 3-D model of the device. Alternatively, 3-D data may be input to the computer 1202*a* for aiding in designing the digital representation of the 3-D device. The process continues to step 1410, where information is sent from the computer 1202*a* to an additive manufacturing device, such as additive manufacturing device 1206. Next, at step 1415, the additive manufacturing device 1206 begins manufacturing the 3-D device by performing an additive manufacturing process using suitable materials. Suitable materials include, but are not limited to polypropylene, thermoplastic polyurethane, polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, resorbable materials such as polymer-ceramic composites, and other similar suitable materials. In some embodiments, commercially available materials may be utilized. These materials may include: DSM Somos® series of materials 7100, 8100, 9100, 9420, 10100, 11100, 12110, 14120 and 15100 from DSM Somos; ABSplus-P430, ABSi, ABS-ESDI, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, CobaltChrome and Stainless Steel materials; Maranging Steel; Nickel Alloy; Titanium; the PA line of materials, PrimeCast and PrimePart materials and Alumide and CarbonMide from EOS GmbH. Using the appropriate materials, the additive manufacturing device then completes the process at step 1420, where the 3-D device is generated.

Using a process such as process 1400 described in connection with FIG. 14, an adaptive surface surgical guiding apparatus may be manufactured using additive manufacturing techniques. Using an additive manufacturing process such as process 1400 allows for an adaptive surface surgical guiding apparatus to be manufactured with rigid portions and variable deformable portions. Various specific additive manufacturing techniques may be used to produce an adaptive surface surgical guiding apparatus. As explained above, these techniques include selective laser sintering, stereolithography, fused deposition modeling, or a foil-based technique. Utilizing these and other additive manufacturing techniques, the entire surgical guiding apparatus may be produced without requiring the separate manufacture and assembly of various different parts.

The invention disclosed herein may be implemented as a method, apparatus, or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

It will be appreciated by persons skilled in the art that numerous variations and/or modifications may be made to the invention without departing from the spirit or the scope of the invention as broadly described. The above described embodiments are, therefore, to be considered in all respects as illustrative and not restrictive.

The invention claimed is:

1. A method of using a surgical guide in a surgical procedure on an anatomical subject, the method comprising:
attaching a surgical guiding apparatus to a first region of an anatomical surface of the anatomical subject so the surgical guiding apparatus directly contacts the first region of the anatomical surface, the anatomical surface being a tissue that is harder than soft tissue;
inserting a soft tissue-piercing element through an aperture of a soft tissue-piercing element attachment;
piercing soft tissue overlying a second region of the anatomical surface with the soft tissue-piercing element until the soft tissue-piercing element contacts the second region of the anatomical surface without piercing the anatomical surface comprising the tissue that is harder than the soft tissue;
contacting the soft tissue-piercing element to the second region of the anatomical surface without piercing the anatomical surface comprising the tissue that is harder than the soft tissue; and
verifying the position of the surgical guiding apparatus using a depth indicator associated with the soft tissue-piercing element attachment.

2. The method of claim 1, further comprising attaching a variable deformable portion of the surgical guiding apparatus to a third region of the anatomical surface.

3. The method of claim 1, wherein the depth indicator comprises markings on the soft tissue-piercing element attachment.

4. The method of claim 1, wherein the soft tissue is not dermis or epidermis.

5. The method of claim 1, wherein the soft tissue is at least one of muscle, tendon, ligament, or fat.

6. The method of claim 1, wherein the second region of the anatomical surface is not altered when piercing the soft tissue.

7. The method of claim 1, wherein the depth indicator comprises markings on the soft tissue-piercing element.

8. The method of claim 1, wherein the soft tissue-piercing element comprises a pin.

9. The method of claim 1, wherein the soft tissue-piercing element attachment is integral to the surgical guiding apparatus.

10. The method of claim 1, wherein the soft tissue-piercing element and soft tissue-piercing element attachment are off-the-shelf devices.

11. The method of claim 1, wherein the soft tissue-piercing element and soft tissue-piercing element attachment are patient-specific devices.

12. The method of claim 1, wherein the soft tissue-piercing element attachment is removably affixed to the surgical guiding apparatus.

13. The method of claim 1, wherein the soft tissue-piercing element attachment is removably affixed to the surgical guiding apparatus by a slot in the surgical guiding apparatus.

14. The method of claim 1, wherein the soft tissue-piercing element attachment comprises a deformable member.

15. The method of claim 14, wherein the deformable member is a spring.

16. The method of claim 1, wherein the surgical guiding apparatus comprises a material suitable for additive manufacturing, and the soft tissue-piercing element comprises one of stainless steel and titanium.

17. The method of claim 1, wherein piercing the soft tissue overlying a second region of the anatomical surface with the soft tissue-piercing element comprises piercing the soft tissue without piercing skin.

18. A surgical guide comprising:
a surgical guiding apparatus, comprising one or more rigid portions configured to attach to a first region of an underlying anatomical surface comprising a tissue that is harder than soft tissue;
a soft tissue-piercing element; and
a soft tissue-piercing element attachment configured for connecting the soft tissue-piercing element to the surgical guiding apparatus, the soft tissue-piercing element attachment comprising a deformable member, wherein the soft tissue-piercing element is biased by the deformable member such that the soft tissue-piercing element is configured to pierce soft tissue overlying a second region of the underlying anatomical surface and not to pierce the tissue that is harder than soft tissue.

* * * * *